United States Patent [19]
Denzer

[11] Patent Number: 6,007,836
[45] Date of Patent: Dec. 28, 1999

[54] TRANSDERMAL VASODILATOR

[75] Inventor: Eric L. Denzer, Melville, N.Y.

[73] Assignee: Vericade, Inc., Melville, N.Y.

[21] Appl. No.: 09/081,176

[22] Filed: May 19, 1998

Related U.S. Application Data

[60] Continuation-in-part of application No. 08/485,633, Jun. 7, 1995, abandoned, which is a division of application No. 08/238,381, May 12, 1994, abandoned, which is a continuation-in-part of application No. 08/069,976, May 28, 1993, Pat. No. 5,333,621.

[51] Int. Cl.[6] .................. A61F 13/00; A61F 13/02; A61F 6/04; A61F 6/02; A61F 5/00
[52] U.S. Cl. .................. 424/449; 424/448; 128/844; 128/842; 128/918; 600/38
[58] Field of Search .................. 424/449, 448

[56] References Cited

U.S. PATENT DOCUMENTS

| | | | |
|---|---|---|---|
| Re. 31,454 | 12/1983 | Hymes | 128/641 |
| 2,577,345 | 12/1951 | McEwen | 128/294 |
| 2,586,674 | 2/1952 | Lonne | 128/294 |
| 2,600,212 | 6/1952 | Dal Borgo | 25/156 |
| 3,136,417 | 6/1964 | Clinch | 206/63.2 |
| 3,339,546 | 9/1967 | Chen | 128/156 |
| 3,677,225 | 7/1972 | Czirely | 128/132 |
| 3,742,951 | 7/1973 | Zaffaroni | 128/268 |
| 3,759,253 | 9/1973 | Cray | 128/79 |
| 3,998,215 | 12/1976 | Anderson et al. | 128/2.06 E |
| 4,119,904 | 10/1978 | Micklus et al. | 128/132 |
| 4,127,118 | 11/1978 | Latorre | 128/79 |
| 4,254,145 | 3/1981 | Birnbaum | 424/305 |
| 4,274,420 | 6/1981 | Hymes | 128/641 |
| 4,291,015 | 9/1981 | Keith et al. | 424/28 |
| 4,306,551 | 12/1981 | Hymes et al. | 128/156 |
| 4,307,717 | 12/1981 | Hymes et al. | 128/156 |
| 4,354,494 | 10/1982 | Hogin | 128/294 |
| 4,415,548 | 11/1983 | Reddy | 424/28 |
| 4,421,737 | 12/1983 | Ito et al. | 424/28 |
| 4,475,910 | 10/1984 | Conway et al. | 604/352 |
| 4,573,996 | 3/1986 | Kwiatek | 604/897 |

(List continued on next page.)

FOREIGN PATENT DOCUMENTS

| | | | |
|---|---|---|---|
| 370482525 | 8/1988 | Germany | C07C 177/00 |

OTHER PUBLICATIONS

US Pharmacopeia, *Complete Drug Reference* 1995 Edition, pp. 1342.

Merck Research Laboratories Division of Merck & Co., Whitehouse Station, NJ *The Merck Index* 1996, pp. 1206, 1252, 1352, 1353, 1354.

Medical Economics Co., Inc. Montvale, NJ *Physicians Desk Reference* 1998, pp. 1494/95, 1893/94.

Cleary, Gary *Cosmetics & Toiletries* Allured Publishing Corp. 1991, Transdermal Drug Delivery.

Woolley, Suzanne, *Business Week*, Jan. 22, 1990 Health—Helping the Medicine Go Down or In. p. 84.

Erickson, Deborah *Scientific American* V 265 Nov. 1991, p. 128+.

*USA Today*, Feb. 1992, pp. 14–15. Skin Patch Fights Cancer's Agony.

(List continued on next page.)

*Primary Examiner*—Thurman K. Page
*Assistant Examiner*—Todd D Ware
*Attorney, Agent, or Firm*—Alfred M. Walker

[57] ABSTRACT

A vasodilator delivery system is provided for producing and maintaining the erection of a male penis during intercourse. The vasodilator is contained in a transdermal patch. The transdermal patch comprises a thin, smooth-edged layered structure for dispensing a suitable vasodilator to the penis skin surface. In each embodiment of the patch, a vasodilator is applied to the skin of the user and is sealed against unwanted contraindicated leakage and contact with the internal tissues of a sex partner.

17 Claims, 5 Drawing Sheets

U.S. PATENT DOCUMENTS

| | | |
|---|---|---|
| 4,638,043 | 1/1987 | Szycher et al. .......................... 528/75 |
| 4,638,790 | 1/1987 | Conway et al. .................... 128/138 R |
| 4,640,688 | 2/1987 | Hauser ................... 604/352 |
| 4,661,105 | 4/1987 | Gale ........................ 604/897 |
| 4,675,009 | 6/1987 | Hymes et al. .......................... 604/304 |
| 4,687,771 | 8/1987 | Gamble et al. ........................ 514/253 |
| 4,704,282 | 11/1987 | Campbell ................................ 424/449 |
| 4,798,600 | 1/1989 | Meadows ................................ 604/347 |
| 4,801,587 | 1/1989 | Voss et al. .............................. 514/248 |
| 4,829,991 | 5/1989 | Boeck ...................................... 128/79 |
| 4,830,854 | 5/1989 | Copelan .................................. 424/445 |
| 4,840,952 | 6/1989 | Gamble et al. ........................ 514/253 |
| 4,849,226 | 7/1989 | Gale ........................................ 424/448 |
| 4,869,723 | 9/1989 | Harmon .................................. 604/349 |
| 4,931,445 | 6/1990 | Goldstein et al. ..................... 514/252 |
| 5,059,603 | 10/1991 | Rubin ...................................... 514/264 |
| 5,124,158 | 6/1992 | Ruwart et al. .......................... 424/449 |
| 5,137,032 | 8/1992 | Harmon .................................. 128/884 |
| 5,147,855 | 9/1992 | Gozes et al. ............................. 514/12 |
| 5,152,997 | 10/1992 | Ebert et al. ............................. 424/449 |
| 5,177,070 | 1/1993 | Katz ........................................ 514/215 |
| 5,219,885 | 6/1993 | Frolich et al. .......................... 514/530 |
| 5,244,677 | 9/1993 | Kreckel et al. ......................... 424/448 |
| 5,270,323 | 12/1993 | Milne, Jr. et al. ...................... 514/309 |
| 5,333,621 | 8/1994 | Denzer .................................... 128/884 |
| 5,488,059 | 1/1996 | Buhl ........................................ 514/349 |
| 5,565,466 | 10/1996 | Gioco et al. ............................ 514/280 |

OTHER PUBLICATIONS

Fields, Holland *Good Housekeeping* v 208 Feb. 1989 p. 163/4.

Rodale, Heidi, *Prevention* (Emmaus, Pa.) v 40 Jan. 1988 pp. 76–81.

Brown, Corie *Business Week* Nov. 16, 1987 p. 153.

McCarthy, Paul *Health* (NY, NY) v 19 Nov. 1987, p. 29.

SerVaas, Cory *The Saturday Evening Post* v 259 Jan./Feb. 1987 pp. 52–54.

Manley, Harriet, *Good Housekeeping* v 203 Aug. 1986 p. 191.

Clark, Matt *Newsweek* v 107 Jun. 30 1986 p. 69.

Cowley, Jeffrey *Newsweek* Sep. 16, 1996 pp. 68–77.

Gourse, Leslie *Science 85* v 6 Oct. 1985 p. 79.

Kaplan, Gary M. *Nation's Business* v 73 Aug. 1985 p. 25.

Blakeslee, Sandra *NY Times* Jun. 2, 1993 Health Section.

*NY Newsday* Jul. 7, 1995 p. A16 FDA Oks Treatment for Impotence.

*NY Newsday*, May 23, 1998 Cover Story Proceed with Caution, p. A5.

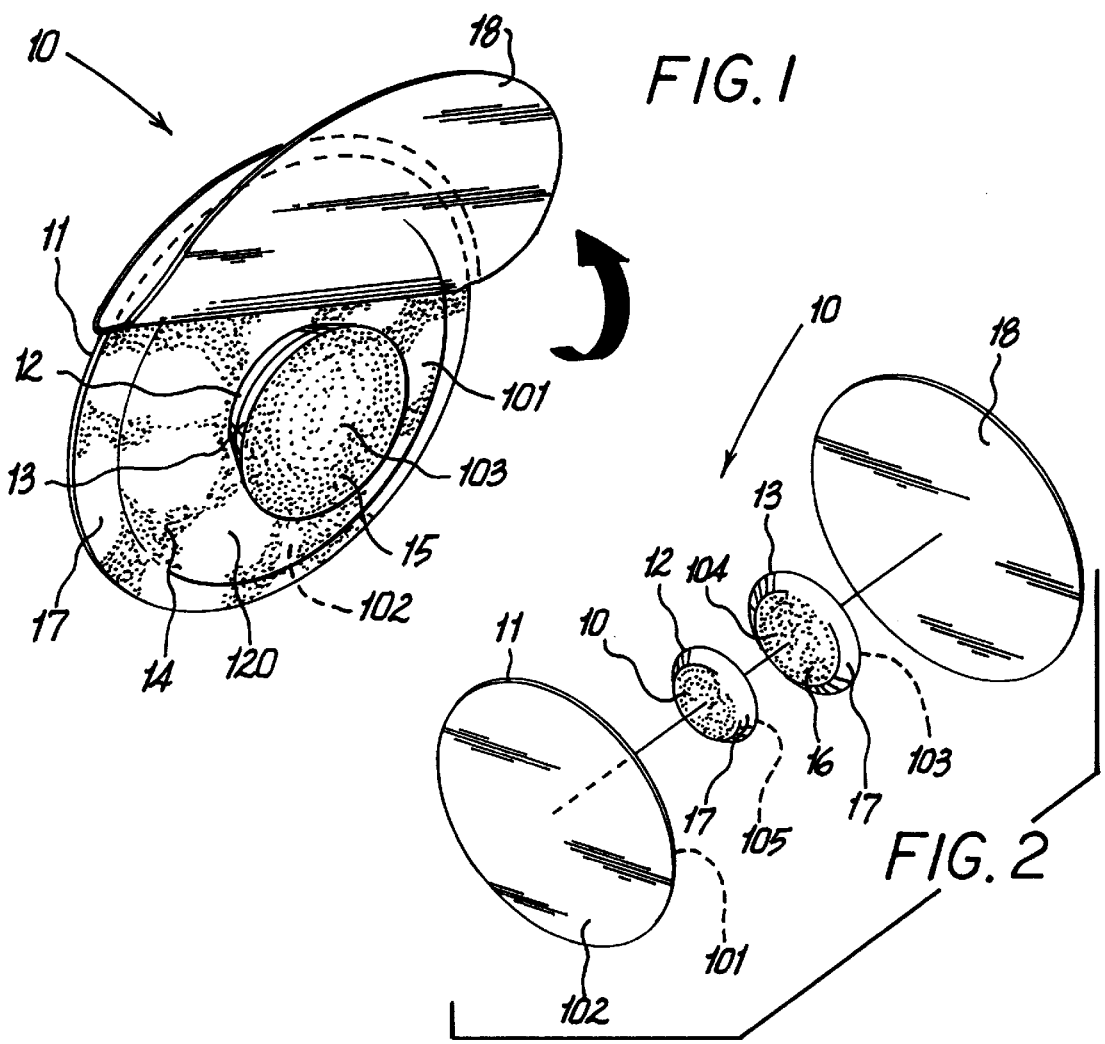
FIG. 1
FIG. 2
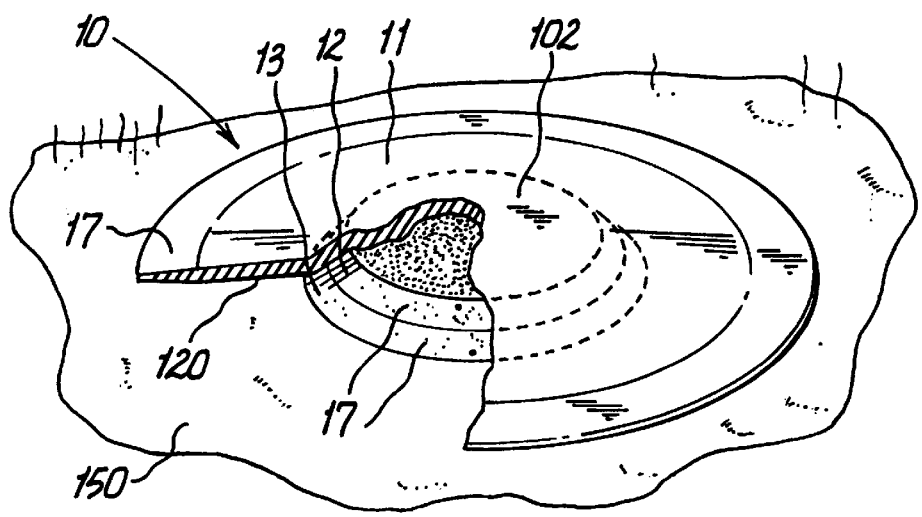
FIG. 3

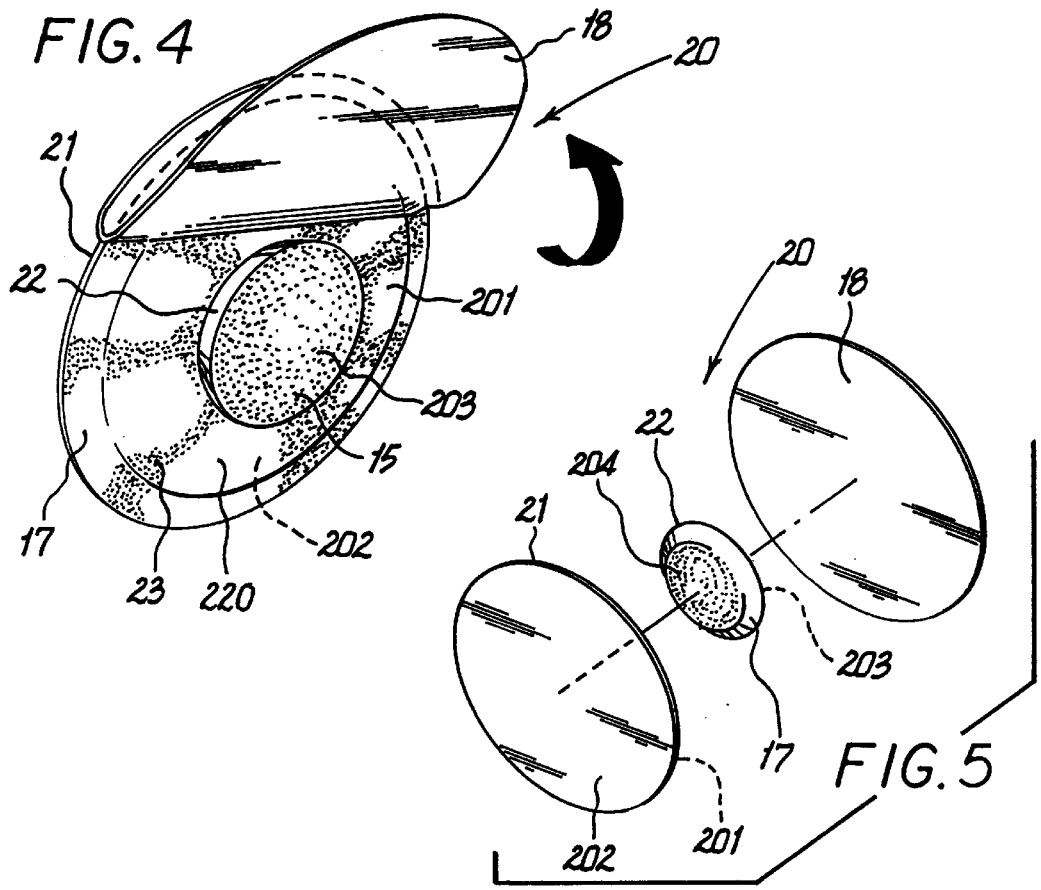
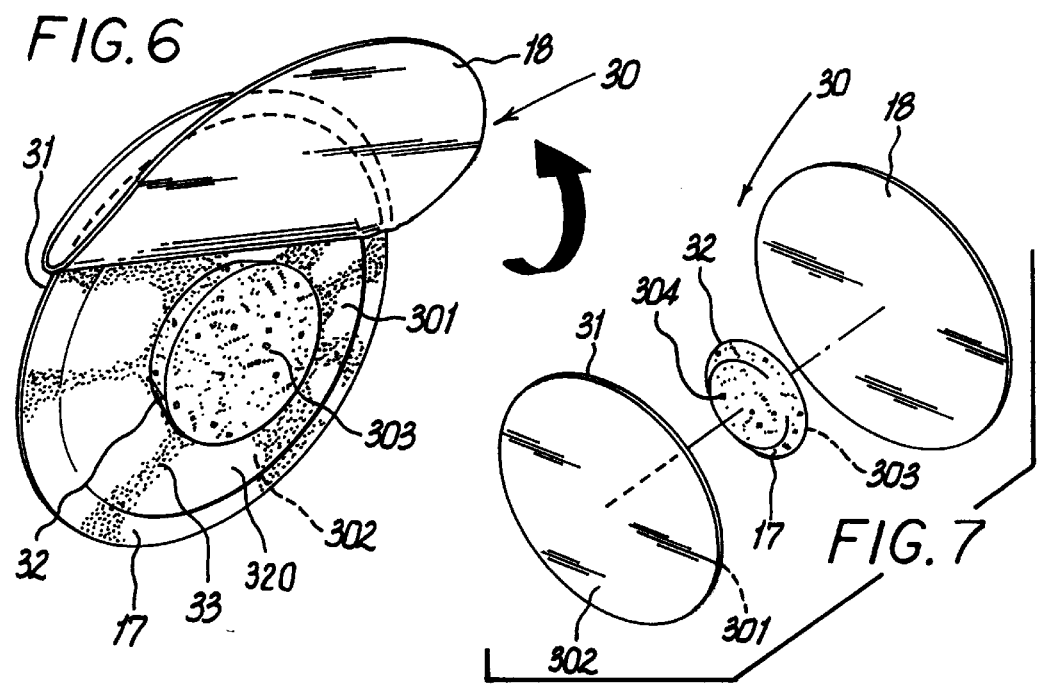

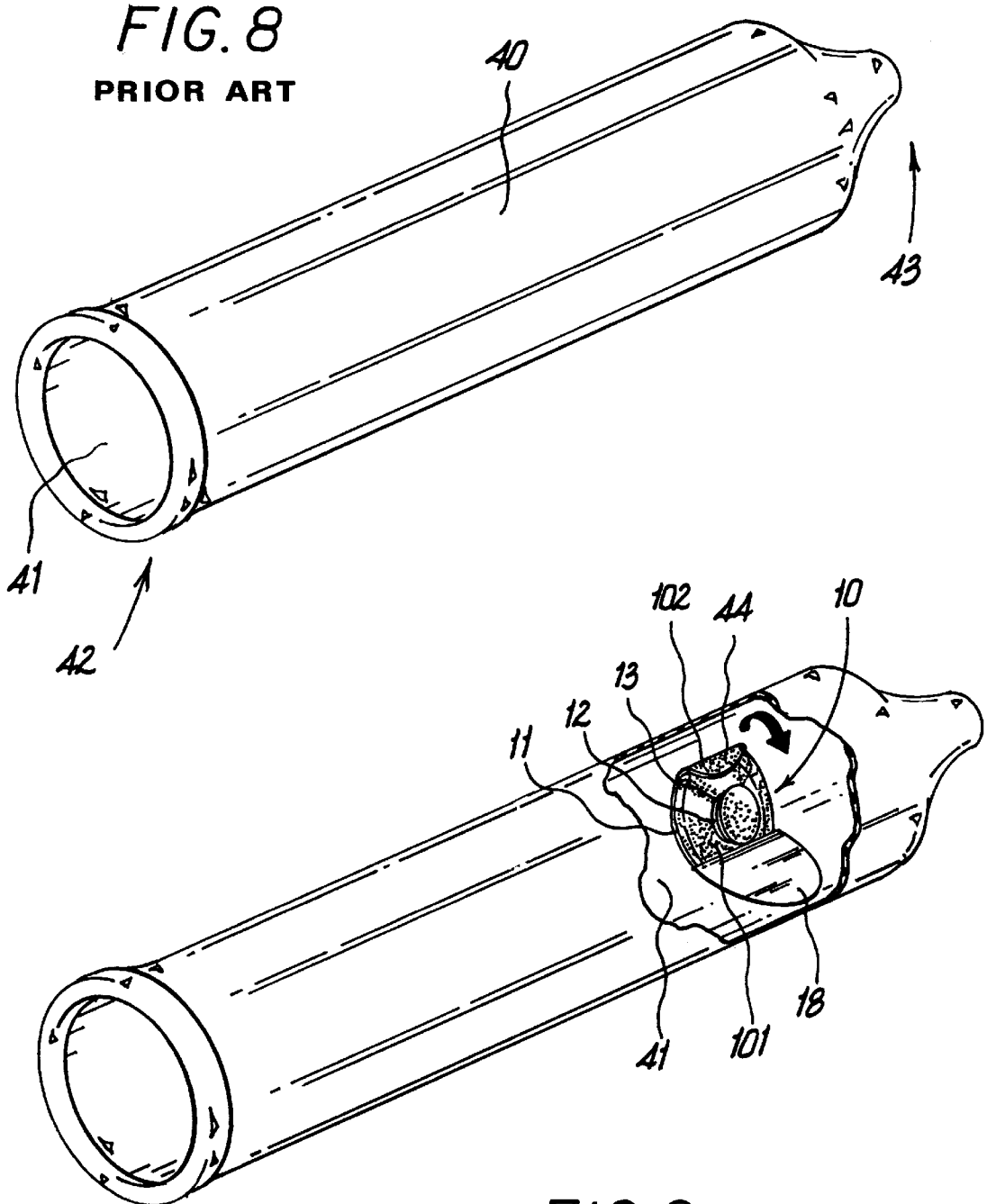

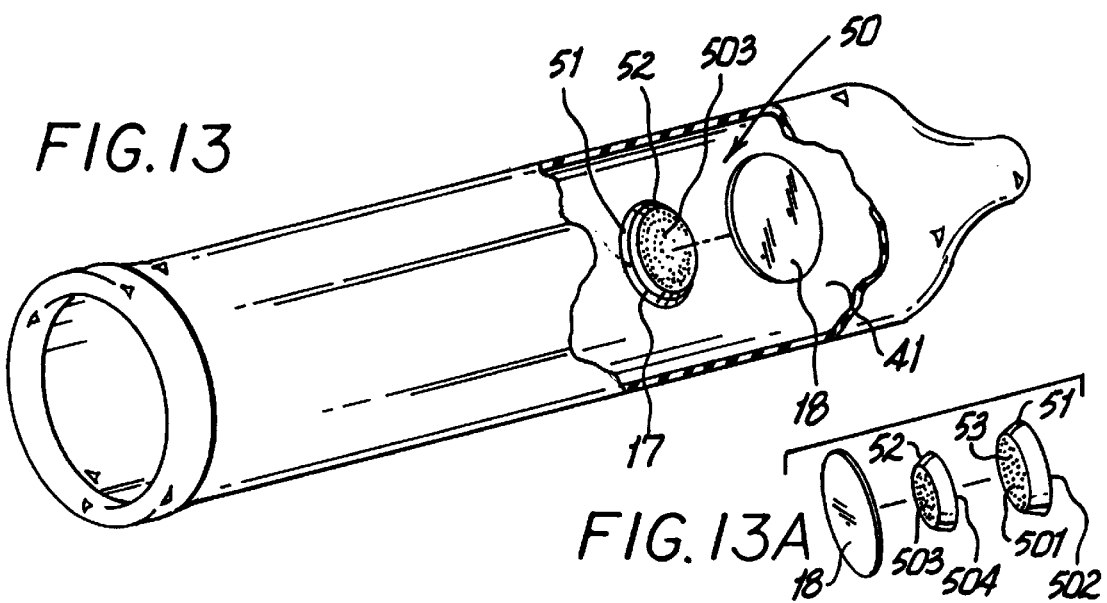
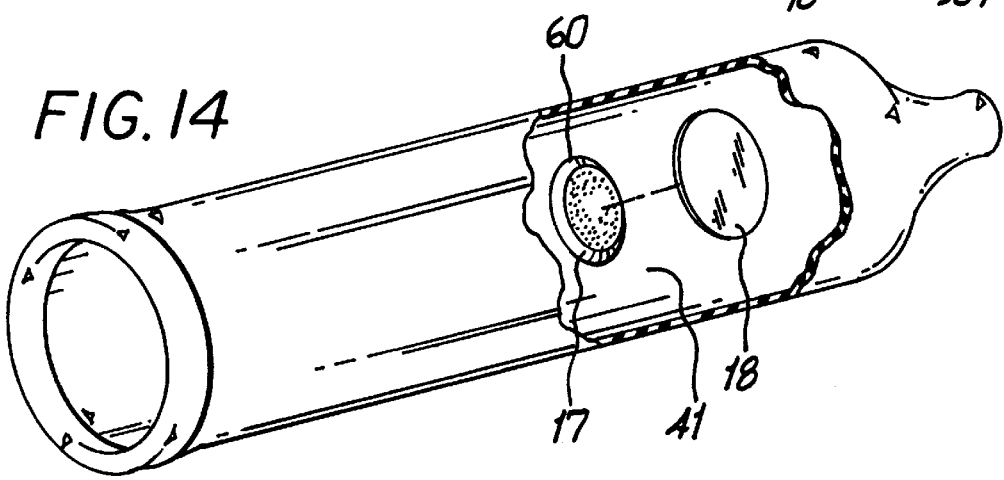
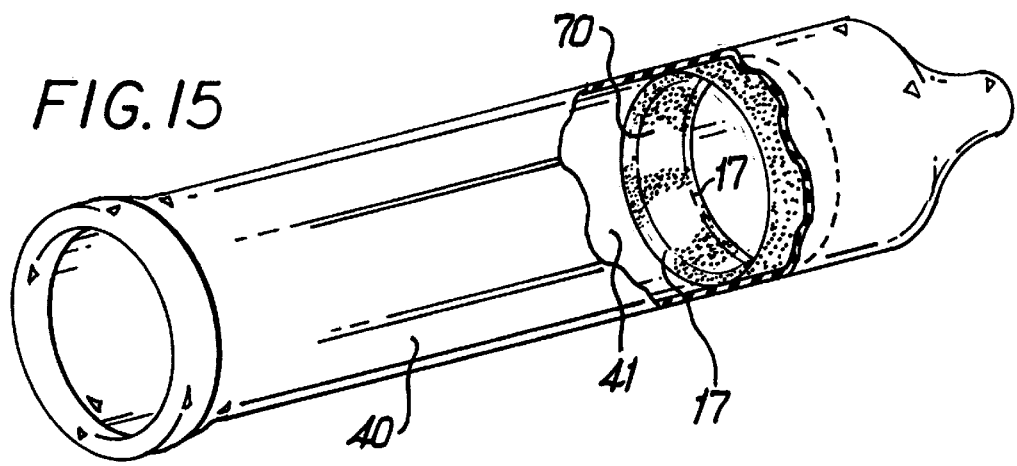

6,007,836

1

TRANSDERMAL VASODILATOR

This application is a continuation-in-part of application Ser. No. 08/485,633, filed Jun. 7, 1995, abandoned, which application is a divisional of application Ser. No. 08/238,381, filed May 12, 1994, which is a continuation-in-part of application Ser. No. 08/069,976, filed May 28, 1993, now U.S. Pat. No. 5,333,621.

FIELD OF THE INVENTION

The present invention relates to providing the ability to engage in sexual intercourse on demand for males having difficulty developing or maintaining penile erection, while isolating the inner tissues of the sex partner from contact with the active pharmaceutical agents used to counteract male impotence. For example, the active pharmaceutical agents may cause hemorrhaging in the female reproductive system.

The present invention provides an impermeable peripheral boundary which physically isolates the active pharmaceutical agent away from the female reproductive system.

Moreover, the present invention eliminates the need for painful conventional subcutaneous injections of pharmaceutical agents to treat male impotence, and is an alternative to orally ingested drugs.

BACKGROUND OF THE INVENTION

It is medically well known that there are many causes of male impotence, but that one potential solution to the problem of impotence is to provide dilation of the blood vessels of the penis in order to provide an erection.

Consequently, a reliable method of providing penile vasodilation is needed. It is well known that there are a number of pharmaceutically active vasodilator materials. Among vasodilators known for producing penile erection by injection are, individually or in combination, papaverine, phentolamine, and prostaglandin E-1. A combination of the three aforementioned vasodilators is apparently preferred for medically injecting into the penis to produce erection. One such combination provides 4.4 mg Papaverine, 0.15 mg phentolamine and 1.5 mcg Prostaglandin in an injection comprising a 0.25 cc volume. Papaverine has been medically injected into a male penis for producing erection in doses from 30–120 mg.

Vasodilators thus being known for clinically producing erections, there remains to be developed a system of delivery of an effective vasodilator, such as prostaglandin, without the need for a painful injection into the male user. A system of drug delivery which has become known is the use of transdermal patches to deliver pharmaceutical materials percutaneously.

Such transdermal patches are known for assisting users to quit smoking, as with NICODERM\ of Marion Merrell Dow Inc. of Kansas City, Mo. 64114 or HABITROL\ of Basel Pharmaceuticals, Division of Ciba-Geigy Corp., Summit, N.J. 07901. NICODERM\ is a nicotine transdermal system in which the user attaches a medication-containing patch to the skin for varying time periods over several weeks. The patches comprising the system contain medication in varying doses. HABITROL\ includes a patch having an adhesive layer attached to a patch having an imbedded pad soaked with a solution of nicotine.

U.S. Pat. No. 5,124,158 of Ruwart describes transdermal antisecretory agents for gastrointestinal disease.

Such transdermal patches have advantages over oral administration of medications, in that the transdermal medi-

2 cation is not interfered with by gastric acids or enzymes, nor does the liver have the ability to interfere during the effective period of drug administration. Transdermal patches are generally layered structures, with the bottom-most, skin-facing layer comprised of an adhesive having microholes. Above this adhesive layer is a medication-containing layer, and a waterproof cover layer is generally provided. The adhesive serves to attach the patch to the skin and the medication in the central layer is provided to the skin through the microholes in the adhesive layer. The medication enters the bloodstream by percutaneous absorption, or, in common parlance, transdermal penetration. A further advantage of the patches is that, to an important extent, they reduce or eliminate user mistakes and forgetfulness. In addition, transdermal patches provide slow-release, measured medication over a period of time much longer than would be available if similar medication were taken orally.

Transdermal patches have been discussed for use with cancer patients ("Skin Patch Fights Cancer's Agony", USA Today, V. 120, p. 14–15, February 1992) to treat diabetics ("Skinside Out", by Deborah Erickson, Scientific American, V. 265, p. 128+, November, 1991) for cardiac patients ("Helping The Medicine Go Down-Or In", by Suzanne Wooley, Business Week, p. 84, Jan. 22, 1990; L. Gourse, "Patchwork Medicine", Science 85, V. 6, P. 79+, October 1985; Kaplan, G. "This Won't Hurt-Really", Nation's Business, V. 73, p. 25, August 1985) and to treat hormonal symptoms ("The Anti-Aging Patch for Women" Good Housekeeping, by S. Fields et al., V. 208, p. 163–164, February 1989; "Patching Up Your Health", Prevention, by Heidi Rodale, (Emmaus, Pa.) V. 40, p. 76–81, January 1988; "Hot Flash!", P. McCarthy, Health, (New York, N.Y.) V. 19, p. 29, November 1987; "More About Estrogen Skin Patches", Saturday Evening Post, (C. Servaas) V. 259, p. 52–54, January/February 1987, Newsweek, V. 107, p. 69, Jun. 30, 1986), and transdermal patches have even been discussed for use in administering cosmetics and perfume. (Corie Brown, "From Making Hearts to Winning Them", Business Week, p. 153+, Nov. 16, 1987).

In "New Way to Take Medicine", Good Housekeeping, V. 203, p. 191, August 1986, author Harriet Manley discusses the mechanism by which medication flows from the patch to the skin.

In "Transdermal Drug Delivery", Cosmetics & Toiletries, V. 106, P. 97, May, 1991, author Gary W. Cleary discusses methodology, applicable models (including the various types of transdermal patches), and the factors of importance in skin permeation.

Other literature discussing transdermal patches includes "Patching Up Drug Deliveries", Newsweek, V. 107, P. 69, Jun. 30, 1986, by M. Clark, and "New Technology Allows Medicine Without Pills", Jet, V. 69, p. 20, Jan. 20, 1986.

Nowhere in the prior art has there been a combination of a vasodilator and a transdermal patch for providing male erections, wherein the vasodilator is administered in through a selected patch which contains an edgewise peripheral impermeable boundary, or is isolated within the inside of a condom, to prevent direct contact of the vasodilator with the woman's female reproductive system. By isolating the vasodilator away from direct contact with the woman's fragile vaginal tissues, the threat of hemorrhaging within the vagina and surrounding reproductive organs is eliminated.

With this new and useful combination of elements, a third natural element in producing male erections for sexual intercourse is the well known use of condoms. Condoms are increasingly important in preventing the spread of sexually transmitted diseases, and, with the present invention, they will serve to provide enhanced, hygienic and safe sexual activity for men who otherwise are unable to have sex.

U.S. Pat. No. 2,577,345 of McEwen discloses a prophylactic condom having a reinforced cap to prevent breakage of the condom at the tip of the condom. U.S. Pat. No. 2,586,674 of Lonne discloses a prophylactic condom with reinforced annular extensions for structural integrity of the condom.

U.S. Pat. No. 3,136,417 of Clinch discloses a method of treating the surface of a condom with a lubrication oil deposited upon the surface of the condom. U.S. Pat. No. 2,600,212 of Dal Borgo describes a method of applying a layer upon a surface with the application of heat. U.S. Pat. No. 3,339,546 of Chem discloses a patch bandage in general. U.S. Pat. No. 3,677,225 of Czirely describes a shortened condom which is adhesively attached to the skin.

U.S. Pat. No. 3,998,215 of Anderson discloses a hydrogel pad attachable to the skin for electro stimulation treatment of injured body limbs. U.S. Pat. No. 4,119,094 of Micklus describes a condom which is coated for a low coefficient of friction. U.S. Pat. No. 4,274,420, U.S. Pat. Nos. 31,454, 4,306,551 and 4,307,717 of Hymes disclose substrate pads for attaching to the skin as electrodes or bandages. U.S. Pat. No. 4,354,494 of Hogin discloses a condom with an annular ring strap to hold the condom in place.

U.S. Pat. No. 4,475,910 of Conway describes a condom catheter having an adhesive to prevent leakage during urinary medical tests. U.S. Pat. No. 4,638,790, also of Conway describes a condom having an adhesive to maintain the condom in place. U.S. Pat. No. 4,415,548 of Reddy discloses a condom saturated with a spermacide solution. U.S. Pat. No. 4,640,688 of Hauser describing a urinary catheter with a pressure adhesive. U.S. Pat. No. 4,798,600 of Meadows discloses a condom with structural parts.

U.S. Pat. No. 4,869,723 of Harmon describes a condom with adhesive to hold the condom in place. Furthermore, U.S. Pat. No. 5,137,032 also of Harmon discloses a condom with adhesives to hold the condom in place.

Moreover, U.S. Pat. No. 5,137,032 of Harmon describes a condom having internally sprayed spermacide medicine, and auxiliary texturized portions to increase stimulation, but does not suggest the use of a transdermal patch within a condom, wherein the transdermal patch emits a vasodilator directly to the skin.

U.S. Pat. No. 4,829,991 to Boeck teaches a vasodilator such as nitroglycerine coated onto the inner surface of a condom for producing a penile erection. The problems with Boeck which are solved by the present invention are (1) that nitroglycerine is generally not an effective vasodilator for producing a penile erection; and (2) a major danger in using the invention of Boeck is that indiscriminate coating of the inner condom surfaces with vasodilator creates a risk of unwanted exposure of the users sex partner to the vasodilator—with potentially dangerous results for the sex partner.

With Boeck, a female sex partner could be exposed to unwanted inadvertent percutaneous vasodilator absorption if the condom ruptures or comes off during sexual intercourse. In addition, if the male condom user of Boeck's invention is not careful in applying and removing the invention, inadvertent female exposure to the vasodilator could occur.

The manner in which the present invention solves Boeck's problem of contraindicated sex partner exposure to vasodilator is to provide a transdermal vasodilator patch for a male user with or without a condom. The patch of the present invention contains the vasodilator in a sealed system, permitting it only to come in contact with the skin of the male user for desired percutaneous transdermal absorption.

Furthermore, nowhere in the prior art is there discussed the use of discreetly obscuring the view of a vasodilator patch for male erections, by secreting the patch within the condom, for example, or adhered to the skin of the male scrotum, but in any case discretely out of view from a sex partner to avoid embarrassment to the male user. Harmon also discusses adhesives for use in condoms. The adhesive can comprise any well known sticky surgical grade adhesive or other pressure sensitive adhesive known to the art, applied by any conventional means, for example as more particularly described in U.S. Pat. Nos. 4,638,790 and 4,475,910.

Additional prior art includes U.S. Pat. No. 4,254,145 of Birnbaum, which teaches the sustained protracted topical drug delivery of prostaglandin, from a transdermal bandage over a prolonged period of time, such as 24 hours, for a continuous reduction of blood pressure. The other non-prolonged drug delivery methods described in Birnbaum '145 include topical application of a cream or lotion or AQUATAIN® solution on a cotton swab, by oral capsules or injection by needle.

However, the transdermal patch of the present invention is applied immediately upon demand before sexual intercourse, such as within minutes before. Because of the spontaneous nature of sexual intercourse, in the present invention the administration of the vasodilator occurs on demand, such as in the situation of direct injections of vasodilators into a penis, as described in U.S. Pat. No. 4,127,118 of Latorre. In contrast to Latorre '118, the administration of the present invention is painless and it solves a long felt need that has existed since Latorre '118 was published in 1978.

Unlike the demand activation of the present invention, and of Latorre '118, the patch of Birnbaum '145 is delivered over a prolonged 24 hours, which is contraindicated given the spontaneity of sexual intercourse and the need for inducing erection on demand.

Furthermore, other prior art includes U.S. Pat. No. 4,573,996 of Kwiatek and U.S. Pat. No. 4,704,282 of Campbell. However, Campbell '282 is concerned with sustained, protracted release of testosterone over a prolonged period of time, such as 8–24 hours or more, that would overcome the problems associated with low overall levels of testosterone. However, neither Campbell '282 or Birnbaum '145 describe the transdermal application of a vasodilator to induce an erection upon demand before sexual intercourse.

The prior art is unsatisfactory, because the devices described therein do not have an immediate delivery on demand of a vasodilator for inducing an erection, as in Latorre '118 or in the present invention without the painful injection of Latorre '118 and priapism or possible resultant formation of scar tissue and subsequent loss of penile function.

In fact, the prolonged sustained administration of testosterone does not cause an immediate erection on demand before sexual intercourse, as it is directed to raising hormone levels, not to immediate delivery of a vasodilator to engorge penile blood vessels with blood to induce an erection.

To that end, Birnbaum '145 and Campbell '282 are directed to a composition and delivery of a particular medication for sustained, prolonged use with impotence or blood pressure irregularities. Thus, the general use of a sustained, prolonged administration of a medication, in conjunction with a transdermal patch, would be suspect as to their effectiveness or expectation of success, unless they could induce an erection on demand before sexual intercourse.

Simply using testosterone or prostaglandin in prolonged delivery whether similar or not, would therefore not provide any expectation of success.

The use of the transdermal delivered vasodilator on demand before sexual intercourse in the present invention would be discouraged, if not clearly taught away from Birnbaum '145 or Campbell '282.

Other patents concerning "on demand" use of a vasodilator to induce an erection before sexual intercourse, include U.S. Pat. No. 5,488,059 of Buhl which discloses injection of a guanidine vasodilator directly into a penis to induce an erection. Buhl '059 also mentions "transdermal application" but there is no discussion or enabling disclosure for a transdermal patch. In that sense, the word "transdermal" is equated with "topical" administration, such as direct application upon the skin of a medication. See Buhl '059 at column 2, lines 62–67.

Similarly, U.S. Pat. No. 5,270,323 of Milne describes inducing penile erections with vasodilators, but either by injection or topical transdermal delivery. However, the "transdermal delivery" in Milne '323 is topically applied to the penis or by iontophoresis, wherein an electrical current applies a solution to the skin. See Milne '323 at column 4, lines 16–24. In contrast to Milne '323, Applicant's specification at page 1, lines 9–18 discusses that a barrier is needed to avoid direction contamination by a vasodilator of the female genital tissues, with resultant bleeding problems.

While U.S. Pat. No. 5,565,466 of Gioco discusses a transdermal patch for delivery of a vasodilator to induce an erection, it was filed first on Aug. 13, 1993, which is after Applicant's first filed parent patent application filed under Ser. No. 08/069,976 on May 28, 1993.

Also, U.S. Pat. No. 5,059,603 of Rubin discloses topical administration of isoxsuprine and caffeine, and nitroglycerine and caffeine for the treatment of impotence.

However, in Rubin '603, the delivery route is described as topical administration by direct contact from squeeze tubes, spray misters, or lotions and ointments applied by cotton swabs. Rubin '603 does not disclose transdermal patches.

Except for Gioco '466, which was filed on Aug. 13, 1993 after Applicant's parent patent application of May 28, 1993, the other three patents of Buhl '059, Milne '323 and Rubin '603 all point to the need for an "on demand" method of inducing erections without contaminating the internal genital tissues of the user's sexual partner, but none of the three make the extra step of suggesting a transdermal patch.

Moreover, Latorre '118 described the need for an "on demand" method of inducing an erection, but Latorre '118 solved the problem with direct injection of a vasodilator into the penis with its attendant problems of pain, possible infection, possible scar tissue and priapism.

Additional prior art includes the orally ingested pill sold under the tradename VIAGRA®, however it is an oral medication which is systemic, and has been known to cause ocular problems.

As an advancement over the solution of Latorre '118 for an "on demand" method of inducing an erection, what the present invention has done is solve a long felt need in the 19 years since Latorre '118 addressed the same problem with the aforementioned attendant problems.

Therefore the method of the present invention of applying a vasodilator from a transdermal patch for on demand use before sexual intercourse is not described or suggested by the prior art.

OBJECTS OF THE INVENTION

It is an object of the present invention to provide a device for facilitating male erection for sexual intercourse which seals a vasodilator material in contact with the skin of a male user and thereby prevents contact of the vasodilator with the vaginal and other internal reproductive organs of a female sex partner.

It is an object of the present invention to prevent leakage and/or escape of the vasodilator through and/or around the surface and/or the at least one edge of the outer layer of the patch of the present invention, and thereby to prevent contact of a woman's internal reproductive system with the vasodilator.

It is a further object of the present invention to provide a system for conveniently and comfortably providing a male with an erection for sexual intercourse.

It is an object of the present invention to provide a vasodilator material in a penile transdermal patch.

It is a further object of the invention to provide a vasodilator material in a transdermal patch that can be discreetly applied behind the scrotum.

It is a further object of the invention to provide a vasodilator material in a combined transdermal patch and condom.

It is an object of the present invention to provide a user-controlled penile transdermal patch where the user applies manual pressure to release the vasodilator material.

It is a further object of the present invention to provide a discreet transdermal patch within the interior of a condom, out of view.

It is an object of the present invention to provide a user-controlled penile transdermal patch where the user applies manual pressure to engage penis skin adhesive and thereby to control the attachment of the transdermal patch to the penis.

It is an object of the present invention to provide a device for producing a male erection which does not expose a female sex partner to vasodilator material.

Other and further objects of the invention will become apparent as the invention is more fully explained. The foregoing list is provided merely as a series of examples, and is not intended to be exclusive or exhaustive.

SUMMARY OF THE INVENTION

In addition to embodiments used inside of a condom, the present invention comprises embodiments used outside of a condom, and thus requiring no condom at all. The non-condom embodiments will be referred to simply as embodiments. Those embodiments used in combination with a condom, and thus requiring a condom, will be referred to as condom-embodiments.

As a means of consistently describing the features of the present invention, the adhesive itself will not be termed a layer in and of itself. Rather, adhesives will be discussed in the present invention as being coated upon or applied to surfaces comprising the patch. The layers of the patch of the present invention will be described in detail, however.

In this invention, the term 'inside' will be used to describe surfaces facing or closest to the skin of the user. The term 'outside' will describe those portions of the invention which are furthest from the skin of the user, or face away from the skin of the user. Thus, for example, the outer layer of a 3-layer patch is the layer which, when the patch is in use adhered to the skin of the user, is disposed farthest from the skin of the user.

However, each of these layers are not limited to a single layer. For example, the outer layer may be an outer protective barrier layer to prevent abrasions or tearing of the patch, and this at least one outer layer may be covered by a further outer layer, such as a water repellent layer.

The term barrier layer will also be used in this invention to describe the at least one outer layers of the patch since this at least one outer layer comprises an impermeable barrier sealing the vasodilator materials under it and within the confines of the patch. Here the term "under" as 'in under the barrier layer', is used to mean between the barrier layer and the skin of the user, and the term 'under' does not necessarily connote a vertical disposition as used in this context.

Also for example, each of the same aforedescribed at least one outer layers will have two surfaces—an outer surface and an inner surface. The inner surface of each of the outer layers, for example, is the surface of each of the outer layers which faces toward the skin of the user.

All of the following embodiments of the present invention, that is, the non-condom-embodiments and the condom-embodiments, are similar in several ways. They are constructed of suitably thin and flexible materials, so as to be able to bend and conform comfortably with the movement of the surface of the skin.

The transdermal patches are constructed of one or more layers, so that each patch presents at least one edge to the skin of the user. The at least one edge results from the fact that the patch can have a round tabular shape, and thus would have at least one edge. The patch can have any tabular shape, such as a square, oblong or oval, in which case the patch could have more than one edge. The shape of the patch is not critical to the present invention. However, the at least one edge may be tapered, and the edges made smooth, so that the patch presents a surface to the skin of the user which is as smooth and frictionless as possible, thus preventing undesirable abrasion and friction from dislodging the patch adhered to the skin of the user.

In addition, all the patches are provided with an adhesive on the inner, skin-facing surface. The adhesive may be a coating sprayed on, or may be a distinct substrate layer with a tacky surface on both sides. To protect the inner layer of adhesive prior to the application of the patch, all the embodiments are provided with a releasable liner. "This protective liner is a film which is easily removed from the" inner surface of the patch "just prior to application on the skin. A release agent in the form of a thin coating is applied to paper, polymer coated paper, or polymer film, which provides structure to the liner. This release agent is necessary to prevent the" skin-facing adhesive "from sticking to its protective liner. Silicone and fluorocarbon-coated release liners are commonly used in transdermal systems for this reason" (Cleary). As a means of consistently describing the features of the present invention, the release liner will not be termed a layer in and of itself, since it is removed prior to application of the present invention.

All of the non-condom embodiments are constructed with at least one outer, stretchable, impermeable barrier layer composed of polyvinyl, polyethylene, polyester or aluminized polymer films and composite films, or any other suitable, impermeable, stretchable and flexible material. The at least one outer layer extends beyond the perimeter of the underlying layers, and has an adhesive material on the inner surface. The underlying layer or layers of the patch, depending on the embodiment, thus comprise and occupy a central area within the perimeter of and under the outer layer. The at least one outer layer serves as a seal, as further described in detail.

The inner surface of this at least one outer layer is coated with an impermeable adhesive which serves the dual function of anchoring the transdermal patch to the skin of the user and attaching underlying layers to the at least one outer barrier layer. To provide instant anchoring to the skin, the adhesive must adhere aggressively and instantaneously with only very slight pressure. The adhesive can be any well known sticky surgical-grade adhesive, or other pressure sensitive adhesive known to the art, and applied by conventional means. Examples are described in U.S. Pat. Nos. 4,638,790 and 4,475,910.

The patch is designed to contain the vasodilator so as to seal it in and prevent its leakage or escape from the area of intended male user skin contact. It is desirable to prevent any and all contact of the vasodilator with the inner tissues of the sex partner.

Accordingly, the patch, while permitting intended male user skin contact with the vasodilator, is designed with an impermeable outer layer, or barrier layer, to prevent vasodilator escape through the upper surface of the patch, and with an impermeable adhesive to prevent unwanted leakage at or from the at least one edge of the patch as well. Thus the patch provides means for sealing the vasodilator within the central portion of the patch away from the woman's vaginal tissues.

In the first embodiment, i.e., the first non-condom embodiment for use apart from and/or without a condom, the vasodilator is provided within a plurality of layered transdermal patch. Delivery of the vasodilator to the penis is accomplished through percutaneous absorption. In one example, such as a 3-layered embodiment, the three layers comprise at least one outer barrier layer, as described above, at least one middle layer containing the vasodilator, and at least one inner layer. The vasodilator is stored and contained in the at least one middle layer of the transdermal patch, which functions as a vasodilator reservoir conventionally in the manner of transdermal medication patches to deliver the vasodilator to the skin surface when the patch is adhered to the skin of the user.

The at least one middle layer contains the vasodilator in a suitable transdermal vehicle, which, as described in U.S. Pat. No. 5,124,158 to Ruwart et al., may be a liquid, a cream, a gel or a paste, all of which are generally known in the art for transdermal use. Typical transdermal compounds which may be used in the present invention, are polyethylene glycol, propylene glycol, triacetin, propyl carbonate, ethanol and isopropyl myristate. The aforementioned typical transdermal compounds may be contained in a reservoir or alternately can be applied to porous or other materials suitable for preparing a transdermal patch, as Ruwart, U.S. Pat. No. 5,124,158 has described.

The at least one inner layer of the multi-layered patch is typical of similar inner layers of some conventionally constructed layered patches. The at least one inner layer of a 3-layered first embodiment of the present invention comprises a means for dispensing the vasodilator through the skin of the male user, for example, such as a membrane made of plastic in the transdermal patch art, having microholes. The microholes in the membrane provide openings that limit the surface area of the middle, vasodilator-containing layer exposed to the skin of the user, thus regulating the amount of vasodilator available.

In this manner regulated dispensing of vasodilator is achieved, and dispensing may be selectively regulated by regulating the number, spacing and diameter of the microholes to achieve selectable total surface areas for conduction of vasodilator through the membrane for skin surface contact. Such at least one inner layer membrane materials are usually films made from non-woven, woven or foamed polymers, or from films made porous by various techniques, as described by Gary W. Cleary in Transdermal Drug Delivery, Cosmetics and Toiletries, Vol. 106, May 1991.

The inner, skin-facing surfaces of the at least one membrane inner layer is coated with a second, comparatively weaker adhesive, which anchors the at least one inner layer to the skin of the user. The aforementioned adhesive is weaker compared to the strong barrier layer adhesive, which secures the entire transdermal patch system to the skin of the user.

The comparatively weaker, membrane-anchoring adhesive is permeable to allow diffusion of the vasodilator through the comparatively weaker adhesive, so as to permit vasodilator to reach and make contact with the skin of the male user. If diffusion of the vasodilator through this comparatively weaker adhesive failed to occur, the vasodilator could not reach the skin of the user, since the vasodilator is contained in the at least one middle layer of the patch and as such is spaced apart from the skin of the user by the weaker adhesive, among other materials as herein described.

Such adhesives as the aforedescribed comparatively weaker adhesive are known to provide adhesion of the transdermal patch system to the skin, and yet are easily removed without removing any skin or leaving a residue.

Desirable characteristics for such a comparatively weaker adhesive material include the ability to adhere very aggressively to a backing material, e.g., the skin-facing inner surface of the aforedescribed microhole membrane while adhering to a lesser extent to skin. Pressure sensitive adhesives which provide a desirable, relatively weak skin adhesion are viscoelastic materials, which, in solvent-free form, remain permanently "tacky", and are described by Cleary in Transdermal Drug Delivery.

As described above, the construction of the multi-layered transdermal patch, such as a 3-layer patch, provides for the stretchable at least one outer layer to completely cover and seal the at least one middle and inner layers. Thus the vasodilator is contained within the patch and only the skin of the male user is permitted to come in contact with it. The transdermal patch system thus seals and prevents leakage of the vasodilator, and prevents inadvertent unwanted contact of the internal tissues of a female sex partner with the vasodilator. This covering and sealing function of the outer layer of the multi-layered patch, such as a 3-layer patch, is also provided by the at least one outer layers in a 2-layer embodiment of the present invention and a flexible solid embodiment, both of which will be described in detail.

In a second embodiment of the present invention, the vasodilator is provided within a two-layered transdermal patch. The two-layer form is similar to the three-layer form, except that, unlike the 3-layer patch, the 2-layered embodiment has no membrane with microholes to restrict the diffusion of medication to the skin.

Compared to the 3-layered patch, this second, 2-layered embodiment makes a larger amount of vasodilator available to the skin of the user more quickly, since there is no microhole membrane to restrict and regulate dispensing of the vasodilator to the skin.

The two-layer patch has an impermeable outer barrier layer in the same manner as the 3-layered embodiment. Also as with the 3-layered patch, the 2-layered second embodiment is provided with an impermeable adhesive material coated on the inner surface, which faces and adheres to the skin of the user, and a smaller at least one inner layer containing the vasodilator material. The impermeable adhesive coated upon the inner surface of the at least one outer layer serves the dual function of securing the at least one inner layer with vasodilator to the outer layer and also fastening the at least one outer layer to the skin. The at least one inner layer, covered by the at least one outer layer when the patch is in use, is thus secured to the skin by means of the at least one outer barrier layer being adhered to the skin of the user and serving as a broad bandage providing adhesion, anchoring, covering and sealing.

The vasodilator, carried within a suitable transdermal vehicle, is stored and contained in the smaller, inner vasodilator-reservoir layer of the 2-layered transdermal patch. The inner surface of the drug-containing at least one inner layer is coated with a second, comparatively weaker adhesive which is comparatively more easily releasable, and which serves to attach the drug carrying at least one inner layer to the skin of the user. In a fashion analogous to the permeable weaker adhesive of the multi-layered embodiment, such as a 3-layer embodiment, this second adhesive is permeable to permit transmission of the vasodilator from the reservoir layer through the permeable adhesive and thence into direct contact with the skin of the male user. The difference between the 2-layered and 3-layered embodiments is that on the 3-layered embodiment, as above described, the weaker, more releasable adhesive is coated upon the at least one inner surface of the inner layer, which comprises a membrane having microholes. In the 2-layered embodiment, the analogous weaker adhesive is coated upon the vasodilator-containing patch layer itself, since there is no membrane having microholes in the 2-layered embodiment.

In a variant of this 2-layered embodiment, the at least one inner surface of the drug-containing inner layer is not coated with a permeable adhesive, so that the vasodilator drug layer itself directly contacts the skin of the user. As in other embodiments of the present invention, the vasodilator is confined under the at least one outer, barrier layer, which acts as a seal and prevents vasodilator material from escaping the confines of the transdermal patch. The impermeable stronger adhesive anchoring the at least one outer barrier layer to the skin of the user further serves to seal the vasodilator and thus prevents vasodilator leakage laterally from around the sides and the at least one edge of the patch.

The 2-layer patch functions conventionally in the manner of transdermal medication patches to deliver the vasodilator to the skin surface when the patch is adhered to the skin of the user. As in the 3-layered embodiment, the patch itself is suitably thin and flexible, so as to be able to bend and conform comfortably with the movement of the surface of the skin, and the at least one edge of the multiple layers may be tapered so that the patch presents a surface to the skin of the user which is as smooth and frictionless as possible, thus preventing undesirable abrasion and friction from dislodging the patch adhered to the skin of the user.

In the third embodiment, the vasodilator is provided in the form of a flexible solid patch. As in the 2-layered embodiment, the flexible solid patch is constructed of an outer, impermeable barrier layer, and at least one inner layer containing the vasodilator material. As in the first 3-layered and second 2-layered embodiments, the at least one outer layer extends beyond the perimeter of the at least one inner layer.

However, the third, flexible-solid embodiment contains an additional adhesive. The adhesive described in the first and second embodiments is also used in the third embodiment.

For purposes of describing the third embodiment, the adhesive used in the first and second embodiments, and also used in the third embodiment will be termed the first adhesive to distinguish it from the second adhesive which comprises a component of the flexible solid material described here in further detail. The first adhesive, described in detail above, is relatively stronger in adhesive strength than the second adhesive, described in further detail below.

In the third embodiment, unlike the first and second embodiments, the vasodilator material is mixed with a comparatively weak adhesive, and the vasodilator-weak adhesive mixture is spread in a thin, slightly moist layer in the center of the inner surface of the impermeable, at least one outer barrier layer. The vasodilator-weak adhesive mixture comprises a material which has a rubbery texture and is a flexible solid. The adhesive component of the flexible solid may be the same as described in the wart remover transdermal patch known by the trade name TRANS-VER-SAL® in which the flexible solid material is comprised of polyethylene glycol-300 USP, Karaya, propylene glycol USP, and quaternium 15. In the TRANS-VER-SAL® patch the aforedescribed flexible adhesive material is mixed with about 15% salicylic acid for application to the skin for wart removal.

In the third embodiment, as with the first and second embodiments, the at least one outer layer is provided with a coating of a relatively stronger adhesive on its inner surface, as described in detail in the first and second embodiments of the present invention. The stronger adhesive serves the dual function of holding the vasodilator-mild second adhesive mixture to the inner surface of the patch and fastening the patch to the skin.

As with the first and second embodiments, the third embodiment patch itself and the vasodilator material are suitably thin and flexible, so as to be able to bend and conform comfortably with the movement of the surface of the skin. The patch functions conventionally in the manner of transdermal medication patches to deliver the vasodilator to the skin surface when the patch is adhered to the skin of the user.

The vasodilator-mild adhesive mixture comprises the flexible solid material of this third, flexible solid embodiment of the present invention. The mild adhesive of the flexible solid-vasodilator mixture allows the vasodilator to be released for percutaneous absorption through the skin of the male user. The flexible solid comprising the vasodilator and mild adhesive mixture is secured in contact with the skin of the user when this flexible solid embodiment is in use.

Of the embodiments discussed above, the three-layer embodiment provides the greatest control over the rate of dispensing of the vasodilator to the skin of the user. Vasodilator dispensing can be controlled by controlling the permeability of the relatively more releasable milder adhesive coated on the microhole membrane inner surface, by controlling the thickness of the microhole membrane inner layer, and by varying the size, number and spacing of the microholes. Of the multi-layered embodiments, the 3-layer embodiment is the preferred embodiment.

Selective variation and control of the effectiveness of the patch itself may also be achieved by varying the absolute dose of the vasodilator contained in the patch of the present invention and also, separately, by selectively varying the nature of the vasodilator. As pointed out, it is known that individual vasodilator materials such as papaverine produce penile erections, and it is also known to synergistically combine vasodilators such as papaverine, phentolamine and prostaglandin to produce erection.

It is anticipated that the patch of the present invention will be provided in a variety of dosages, comprising a spectrum from small dose to large dose, with said doses to be determined by a treating physician and/or an individual male user. It is anticipated that vasodilator drug choice and dosage for the present invention, as for all medications, will be determined by the usual and well known variety of individual medical considerations in the case of each user.

The present invention is thus provided in a variety of vasodilator drugs, and drug combinations, and also in a variety of dosage strengths, so as to meet the medical requirements of the widest possible spectrum of male users.

In cases when the rate of diffusion needs to be maximized, for example, where fastest possible delivery of vasodilator to user skin is desired, the second embodiment, with an absence of a microhole membrane, is a preferable alternative. This second embodiment may be utilized without an adhesive on the inner surface of the inner layer, thus placing no adhesive and no membrane between the skin of the user and the vasodilator reservoir. Such a no-inner-adhesive variant of the second embodiment produces the fastest vasodilator delivery to the skin among all of the embodiments of the present invention.

All three above described embodiments can be used by affixing to various parts of the users body in the genital area, for instance either at the base of the penis, or behind the scrotum.

The patch of the present invention is manufactured with a conventional release liner material for protecting the adhesive. The release liner is removed by the user just before applying the patch to the skin. The user peels off the release liner from the adhesive of the present invention in the manner of release liner removal from well-known strip bandages. As with strip bandages, light manual pressure will serve to cause adherence of the aforedescribed adhesives to the skin of the user.

When used at the base of the penis, the patch may be manufactured as a strip with rounded ends, placed circumferentially at the base of the penis substantially as an annular ring, or may be any other convenient shape. The patch may be manufactured as a plurality of small round or oval disks, and, if so, preferably as a pair of such disks. These disks are preferably placed at the base of the penis, one on each side, for example, where the plurality is comprised of a pair of such disks.

The material and/or materials of the patch in all three embodiments may be made stretchable to accommodate the distention of the skin adjacent to the at least one inner layer during erection. Alternately, substrate of the at least one inner layer or layers may be made stretchable to accommodate the distention of the skin adjacent to the at least one inner layer during erection. The at least one outer layer may be manufactured of a stretchable plastic or latex.

The patch or plurality of patches would be placed at the sides of the flaccid penis, near the base. As erection is achieved, the stretchable at least one outer layer expands to accommodate the increased circumference and length of the penis, without causing undue constriction or discomfort, and at the same time the at least one outer layer would continue to adhere firmly to the skin of the user.

In addition, the patch has at least one edge, since it is wafer-like in contour, and may be manufactured as a disk, a square, or any useful shape for a medicinal patch. The patch may be provided with a taper in its thickness, so that while its thickness is not great, the thickness is nonetheless tapered toward the at least one edge. The at least one edge is further made smooth. The tapering and smoothness of the at least one edge ensures a substantial absence of friction and mechanical obstruction when the patch moves relative to an adjacent surface.

When used behind the scrotum, the patch may be manufactured as an oval, rounded triangle, or any useful shape for a medicinal patch. Hair in this scrotum area may need to be removed to allow effective contact between the patch and the skin of the user.

In addition to the foregoing discussion of transdermal patch-delivered vasodilator material for producing a penile erection, the present invention also combines a conventional condom-with a transdermal patch-delivered vasodilator pharmaceutical material for generating and maintaining the erection of the penis for sexual intercourse. Delivery of the vasodilator to the penis is accomplished essentially through percutaneous absorption. In the condom-embodiments of the present invention, it is necessary to place the transdermal patch near or substantially at the tip of the condom, where the condom tip may also be identified as the reservoir end, the sealed end, or the distal end for reference. Thus, in the condom-embodiments of the present invention, the transdermal patch will be applied to the penis at, on or near the glans thereof, depending upon user application of the condom-transdermal patch combination.

When used by uncircumcised males, the patch may have to be located behind the foreskin of the user. Nonetheless, in the case of uncircumcised males, the in-condom patch will be disposed within the condom so as to result in placement at, substantially at, or near the glans of the users penis.

The present invention may be manufactured with a suitable marker on the outside of the condom to visually indicate the location of the patch. If concealment so as not to embarrass the male user is desired, the visual marker of patch location in the condom may be absent or dimly distinguished, so that the user may know its location without unduly calling attention visually to the fact that the condom has anything inside of it. Use of a visual marker is not critical to the present invention since the user will have to remove the releasable liner when applying the condom, so he will know where the patch is. In addition, the user will probably be able to feel the patch, even though the patch is stretchable. Also, unless the condom is totally opaque, the patch will be somewhat visible through the condom.

The patches used in all of the condom-embodiments can have any tabular shape, such as a square, oblong or oval, or any other suitable shape. A preferable alternative to a disk, square or other shape of patch in any of the condom-embodiments is to construct the transdermal patch as an annular ring disposed within the condom, preferably disposed so as to be at, substantially at, or near the glans of the user's penis when the patch is in use. The shape of the patch is not critical to the present invention.

The material and/or materials of the patch in all the condom-embodiments may be made stretchable to accommodate the distention of the skin adjacent to the patch during erection.

The first three condom-embodiments of the present invention are similar to the three non-condom embodiments discussed above. Each of the above described non-condom embodiments is provided within a conventional condom. There are differences in the adhesive systems between the condom and non-condom embodiments, and these differences will be described in detail.

In the first condom-embodiment of the present invention, the vasodilator is provided within a three-layered transdermal patch which is similar to the first non-condom embodiment described above, except that the at least one outer surface of the barrier layer is provided with an adhesive which attaches the 3-layer patch to the inner wall of the condom.

The second condom-embodiment of the present invention is similar to the two-layered transdermal patch of the second non-condom embodiment described above, except that the at least one outer surface of the barrier layer is provided with an adhesive which attaches the 2-layer patch to the inner wall of the condom.

In the third condom-embodiment, like the third non-condom embodiment, the vasodilator is provided within a flexible solid transdermal patch, except that the outer surface of the at least one barrier layer is provided with an adhesive which attaches the flexible solid patch to the inner wall of the condom.

As in the case of the non-condom embodiments, a 3-layered condom-embodiment is preferred because it gives the greatest control over the rate of dispensing of the medication, but, in cases where the rate of dispensing needs to be maximized, the second, 2-layered embodiment, without adhesive on the inner surface of the inner layer, is a preferable alternative.

Each of the condom-embodiments described above can be constructed in two variations, each employing a different strength of the adhesive used to attach the patch to the inner wall of the condom.

In the first variation, there is an adhesive system employing adhesives of different strengths for selective release. The adhesive securing the transdermal patch to the condom wall is made releasable, and thus weaker, whereas the adhesive securing the patch to the penis skin is made stronger. When used, the condom wall adhesive releases, while the penis skin adhesive remains secured to the skin of the users penis. The transdermal patch is thereby transferred from the condom wall to adhesive contact with the skin of the user's penis when the patch is put into use.

This selective adhesive system herein described can be user controlled or can function automatically. Where user control is desired, the stronger penis skin adhesive upon the inner surface of the transdermal patch is made pressure sensitive. The user applies manual pressure upon the outside wall of the condom adjacent to the position of the transdermal patch which is inside the condom. The user will know the location of the patch because a suitable visual indicator is provided on the outside wall of the condom adjacent to the location of the patch.

When the stronger adhesive of the inner, skin-facing surface adheres to the skin, the weaker, releasable adhesive securing the patch to the condom wall will thereupon release, allowing the patch to remain on the penis and to move relative to the inside wall of the condom along with the penis.

As with the non-condom embodiments of the present invention, the construction of the patches in these various condom-embodiments is designed to prevent the vasodilator material from contacting the skin of the female during use. Even though the transdermal patch can detach from the inner wall of the condom, each patch is constructed with an impermeable barrier layer which comprises the at least one outer layer of each respective condom embodiment, and the adhesive that anchors the patch to the skin of the penis is designed to remain adhered to the skin of the penis, preventing any lateral leakage of the vasodilator.

In another variation of the various condom-embodiments, the adhesive anchoring the patch to the condom wall is not made releasable. The patch remains attached to the condom wall during use, and the adhesive which attaches the patch to the penis is not made stronger than the adhesive attaching the patch to the condom wall, so that the patch remains attached to both the inner condom wall and the skin during use, and removal of the condom from the penis will result in removal of the patch from penis skin contact as well. Where the use of a condom is favored, this is the preferred design of this embodiment.

In all the various condom-embodiments, the surfaces which will be adjacent to the patch, of course, are (a) the condom wall; and (b) the skin of the penis. In the first variation, the transdermal patch is transferred from the condom wall to the skin of the user's penis by the system of differential adhesives described above. Therefore, in the first variation, the surface adjacent to the patch, relative to which the patch must move, is the inner wall of the condom. The above described thickness taper and smoothness of the at least one edge prevent mechanical tearing of the condom wall due to the relative motion of the patch and the condom wall. In the second variation, the patch remains attached to both of the adjacent surfaces.

The further condom-embodiments of the present invention are similar to each other in that the transdermal patch has no at least one outer, impermeable barrier layer. The wall of the condom itself serves as the barrier, preventing leakage of the vasodilator. As a result, in both the further condom-embodiments, the patch must remain anchored to the inner wall of the condom, so that removal of the condom will result in removal of the patch containing vasodilator as well.

As in all the embodiments heretofore described, the patch may be provided with a taper in its thickness, so that while its thickness is not great, the thickness is nonetheless tapered toward the at least one edge. The at least one edge is further made smooth. The tapering and smoothness of the at least one edge ensures a substantial absence of friction or chafing when the patch is in use.

As with the previously described embodiments, in the further condom-embodiments the patch itself and the vasodilator material are suitably thin and flexible, so as to be able to bend and conform comfortably with the movement of the surface of the skin.

In a further condom-embodiment of the present invention, the vasodilator is provided within a two layered transdermal patch. The at least one outer, condom-facing layer contains the vasodilator in a suitable transdermal vehicle, contained in a reservoir or alternately applied to porous or other materials suitable for preparing a transdermal patch, as previously described. The outer surface of the at least one outer layer is provided with a strong adhesive, which anchors the patch to the inner surface of the condom. The at least one inner, skin-facing layer is a plastic membrane with microholes as previously set forth. The at least one inner layer is held in contact with the skin of the user by a suitable adhesive in accordance with the foregoing discussion and the microholes permit regulated dispensing of the vasodilator from the at least one outer reservoir layer of the patch to the skin of the user.

The two surfaces of the at least one inner membrane layer are coated with a comparatively weak adhesive as follows: the inner surface of the at least one inner membrane layer is anchored to the skin of the user. The outer surface of the at least one inner membrane layer is also adhered to the outer reservoir layer. The aforedescribed weak adhesive is permeable, to allow dispensing of the vasodilator to the skin by diffusion through and across the weak permeable adhesive, as heretofore described.

The second further condom-embodiment of the present invention is analogous to the earlier described flexible solid embodiments. The vasodilator material is mixed with a mild adhesive, and the vasodilator-mild adhesive mixture is spread in a thin, slightly moist layer on the inner surface of the condom. The vasodilator-mild adhesive mixture comprises a material which is a flexible solid, as described in detail above. In the second further condom-embodiment, the inner surface of the condom which will contact the flexible solid is provided with a coating of a stronger adhesive on its inner surface. The stronger adhesive serves the function of adhesively holding the at least one flexible solid layer to the inner surface of the condom, so that removal of the condom will result in removal of the at least one flexible solid layer as well.

The patch functions conventionally in the manner of transdermal medication patches to deliver the vasodilator to the skin surface when the patch is adhered to the skin of the user.

Any of the aforementioned various condom-embodiments may be provided with a suitable lubricant and/or spermacide, such as Nonoxynol-9, or any other suitable lubricant/spermacide. The lubricant/spermacide would coat the entire inner and outer surfaces of the condom. The lubricant/spermacide can be isolated from the vasodilator material and from the adhesive material on the inner, skin-facing surface of the patch by the releasing liner.

The preferred embodiment is a method for treating male impotence by inducing a male penile erection on demand immediately before sexual intercourse, including the steps of applying directly to the skin of a male user in the penile region thereof, such as for example, to the scrotum, immediately prior to sexual intercourse a transdermal patch having adhesive application means for adhering the same to the male user's skin.

The transdermal patch has therein an effective amount of treatment composition such as a vasodilator.

For example, in one embodiment of the present invention, 10 milligrams of phentolamine mesylate is dissolved in 0.230 milliliters of alcohol (ref. *The Merck Index,* Twelfth Edition, 1996, page 1252. An alcohol solution is preferred since aqueous solutions cannot be stored for any length of time. The dosage for an adult of phentolamine mesylate is 5 milligrams (*Physicians Desk Reference*,$52^{nd}$ Edition, 1998, pp 1893–1894). It is assumed that there will be a 50 percent transdermal transfer of the active ingredient across the thin scrotal skin of the penis. The thickness of the textile carrier in the patch is 0.160 inches, and the textile material in the patch is one inch square. The total volume of the solution of 0.10 milligrams of phentolamine mesylate and 0.230 milliliters of alcohol is 0.240 milliliters. Conversion of metric units to units of measurement gives a solution thickness of 0.37 milliliters, or 0.146 inches. The textile carrier contains 91 percent by volume of the solution and 9 percent by volume of the textile material.

Other vasodilators may also be employed, such as papaverine or prostaglandin E-1, or mixture thereof.

The transdermal patch has a dispensing means for dispensing the vasodilator only to the skin of the user in an effective amount sufficient to induce a male penile erection on demand immediately prior to sexual intercourse and a barrier means for preventing contact of the vasodilator material with the internal genital tissues of the male user's sexual partner.

The transdermal patch may include a plurality of layers with an inner layer for contacting the skin of the male user in the penile region including a reservoir for the vasodilator material and the dispensing means therefore, and an outer barrier layer which completely envelopes the inner layer and the reservoirs and extends beyond all the peripheral edges of the inner layer.

Alternatively, the treatment composition includes a vasodilator selected from the group consisting essentially of papaverine, phentolamine and prostaglandin E-1.

The method of producing a male penile erection on demand immediately before sexual intercourse and for reducing friction during sexual intercourse includes the steps of:

a) applying the transdermal patch on demand immediately before sexual intercourse with an adhesive application means for adhering the patch to a male user's skin in the penile region, wherein the transdermal patch includes an inner dispensing layer having the treatment composition comprising the vasodilator;

b) dispensing the vasodilator material only to the skin of a user in the penile region by applying the transdermal patch to the penile region of the user.

The patch further has a barrier means for preventing contact of the vasodilator material with the internal genital tissues of the male user's sexual partner. For example, the patch has a plurality of layers, including an outer layer opposite to the inner dispensing layer. The transdermal patch further has an outside perimeter edge extending around a perimeter of the outer layer and the inner dispensing layer.

The patch includes a means for producing reduced friction and reduced mechanical interference when the patch undergoes movement relative to an adjacent surface of the internal genital tissues of the user's sexual partner with which the patch is in slidable contact during sexual intercourse, such as a smooth, continuous taper of thickness wherein the thickness of the patch is greatest toward a center of the patch and thinnest at the outside perimeter edge.

The patch further may have a middle layer therebetween. Each respective aforementioned layer has an outer surface facing away from the penile region skin of the user and an inner surface facing toward the penile region skin of the user.

The method steps may also further include:

a. providing the outer surface of the outer layer to provide an impermeable barrier layer for sealing the vasodilator within the confines of the patch;

b. providing a middle layer with a reservoir containing the vasodilator;

c. dispensing the vasodilator from the inner layer of the patch through the penile region skin of the male user.

The outer layer has substantially a larger surface area than a surface area of the middle layer and a surface area of the inner layer. The outer layer extends radially beyond the respective exterior edges of the middle and inner layers for sealing the vasodilator within the patch and for sealing the vasodilator in contact with the penile region skin of the user of the patch.

The radial extension of the outer layer extends beyond the dimensions of the middle and inner layers and functions as a peripheral area. The outer layer further has a central area having an outer surface and an inner surface, the middle layer being adhesively attachable to the inner surface of the central area.

The inner surface of the outer layer is coated with a pharmaceutically suitable impermeable adhesive covering the peripheral area of the outer layer as well as the central area thereof, for, respectively, adhering sealably to the penile region skin of the user and adhering to the middle layer of the patch.

The outer surface of the inner layer is adherable to the middle layer by means of a thin coat of a suitable adhesive which the adhesive is permeable to the vasodilator. The inner surface of the inner layer is provided with a coat of an adhesive permeable to the vasodilator, and the adhesives exposed to the penile region skin of the user are provided with a removable protective release liner to be removed before the patch is adhered to the penile region skin of the user.

While the patch is preferably planer, such as circular or square, it may also be an annular sleeve ring.

In addition, the means for dispensing the vasodilator through the penile region skin of the male user may be a plastic film having microholes.

BRIEF DESCRIPTION OF THE DRAWINGS

FIG. 1 is a perspective view of a multi-layered embodiment of the present invention.

FIG. 2 is an exploded view of the embodiment of FIG. 1, with adhesives shown.

FIG. 3 is a perspective cut-away view of the embodiment shown in FIG. 1, installed on a patch of skin.

FIG. 4 is a perspective view of a 2-layered embodiment of the present invention.

FIG. 5 is an exploded view of the embodiment of FIG. 4, with adhesives shown.

FIG. 6 shows a perspective view of the flexible solid embodiment of the present invention.

FIG. 7 shows an exploded view of the flexible solid embodiment of FIG. 6, with adhesive shown.

FIG. 8 is a perspective view of a prior art condom.

FIG. 9 is a cut-away sectional view of a multi-layered condom-embodiment of the present invention.

FIG. 13 is a cut-away, sectional view of another condom-embodiment of the present invention.

FIG. 13A is an exploded view of the condom-embodiment of FIG. 13.

FIG. 14 is a cut-away, sectional view of another condom-embodiment of the present invention.

FIG. 15 shows a cut-away, perspective view of a condom having a transdermal patch in the form of an annular ring disposed near the tip or head end of the condom.

DETAILED DESCRIPTION OF THE DRAWINGS

Figure 10:
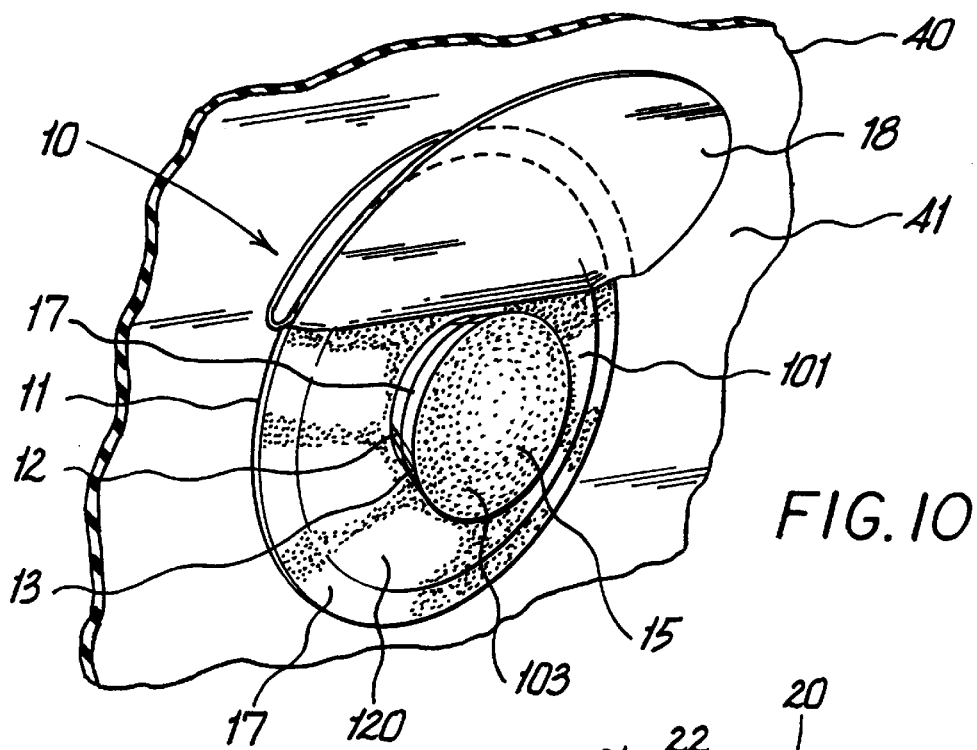
FIG. 10 is an exploded perspective view of the condom-embodiment as in FIG. 9.

The drawings are described in the following manner, with all reference numerals being consistently used throughout the drawings.

FIG. 1 shows a perspective view of a multi-layered transdermal patch 10, for example, such as shown with three distinct layers, (first embodiment of the present invention), having at least one impermeable outer barrier layer 11 having an inner surface 101 facing the skin of the user when the patch is in use, and outer surface 102, facing away from the skin of the user. Inner surface 101 extends circumferentially and radially beyond the inner layers in the manner of a covering. The portion of inner surface 101 which extends circumferentially and/or radially beyond the inner layers is peripheral area 120. Peripheral area 120 is coated with an impermeable sealing adhesive 14 for adhering the patch to the skin and sealing in the vasodilator, and thereby preventing the vasodilator material from spreading beyond the confines of patch 10. Patch 10 is provided with at least one middle layer 12 in which is conventionally contained and stored a vasodilator material for transdermal application to the skin.

At least one middle layer 12 may contain the vasodilator in such conventional arrangements as described in U.S. Pat. No. 3,742,951 of Zaffaroni, U.S. Pat. No. 4,675,009 of Hymes, U.S. Pat. No. 4,638,043 of Szycher, U.S. Pat. No. 5,244,677 of Kreckel or as discussed in Cleary, supra.

At least one middle layer 12 is in contact with both at least one outer layer 11 and at least one inner layer 13. At least one inner layer 13 is constructed of a layer which contains a means for dispensing the vasodilator through the skin of the user, such as, for example a plastic film with microholes, such as described in Clark, "Patching Up Drug Deliveries", Newsweek, Jun. 30, 1986, p. 69. At least one inner layer 13 has an inner skin-facing surface 103 which is provided with a permeable adhesive 15, which anchors the at least one inner layer 13 to the skin. At least one inner layer 13 is in contact with and anchored to at least one middle layer 12 by means of a coat of adhesive shown elsewhere in FIG. 2 of the drawings. Also demonstrated is the tapering 17 of the edges of the at least one outer layer 11, so that patch 10 produces substantially no friction or mechanical interference when the patch undergoes movement relative to an adjacent surface with which the patch may be in slidable contact during sexual intercourse.

Also shown is release liner 18, which covers the inner surface of patch 10, i.e. peripheral area 120 of inner surface 101, as well as inner surface 103 of at least one inner layer 13 so as to protect the respective adhesive-coated surfaces until the patch is to be used. Release liner 18 is shown partially peeled back.

FIG. 2 is an exploded perspective view of the multi-layered patch 10 of FIG. 1, in reversed view. At least one inner layer 13 is anchored to at least one middle layer 12 by an at least one layer of permeable adhesive 16. At least one middle layer 12 has an inner skin facing surface 105 and an outer surface 106 facing away from the skin.

Inner layer 13 has an inner, skin facing surface 103 and an outer surface 104. Outer surface 104 of outer layer 13 is provided with a coating 16 of permeable adhesive, which anchors the at least one inner layer to the at least one middle layer. Also demonstrated is the tapering 17 of the edges of at least one middle layer 12 and one inner layer 13, so that patch 10 produces substantially no friction or mechanical interference when the patch undergoes movement relative to an adjacent surface with which the patch may be in slidable contact during sexual intercourse.

Outer, barrier layer 11 has an inner surface 101 and an outer surface 102. Inner surface 101 is anchored to middle layer 12 by means of an adhesive 14 shown elsewhere in FIG. 1 of the drawings. Also shown is releasable liner 18.

FIG. 3 is a perspective cut-away view of multi-layered patch 10 of FIG. 1, adhered to the skin 150 of a user, showing outer surface 102 of at least one outer layer 11, demonstrating the contact of at least one outer layer 11 with the skin, showing peripheral area 120 of at least one outer layer 11 extending beyond at least one middle layer 12 and at least one inner layer 13, and showing the central location of at least one middle layer 12 and at least one inner layer 13. Also demonstrated is the tapering 17 of the edges of at least one outer layer 11, at least one middle layer 12, and at least one inner layer 13, so that patch 10 produces substantially no friction or mechanical interference when the patch undergoes movement relative to an adjacent surface with which the patch may be in slidable contact during sexual intercourse.

FIG. 4 is a perspective view of 2-layered transdermal patch 20 (second embodiment), having an at least one outer barrier layer 21 which has outer surface 202 and inner, skin-facing surface 201. Inner surface 201 further has peripheral area 220 which extends circumferentially and radially beyond at least one inner layer 22. Peripheral area 220 is coated with an impermeable sealing adhesive 23 for adhering inner layer 22 to outer layer 21, and adhering the patch to the skin and sealing in the vasodilator, and thereby preventing the vasodilator material from spreading beyond the confines of patch 20. Patch 20 is provided with an at least one inner layer 22 in which is contained and stored a vasodilator material for transdermal application to the skin. At least one inner layer 22 has inner skin-facing surface 203 which is provided with a coat of permeable adhesive 15. Also shown is the tapering 17 of the at least one edge of at least one outer layer 21, so that patch 20 produces substantially no friction or mechanical interference when the patch undergoes movement relative to an adjacent surface with which the patch may be in slidable contact during sexual intercourse.

Also shown is release liner 18, which covers the inner surface of patch 20, protecting adhesive-coated surfaces 201 and 203 until the release liner 18 is removed before the patch is adhered to the skin of the user. Release liner 18 is shown partially peeled back. In a variant of this embodiment, permeable adhesive coating 15 may be omitted.

FIG. 5 is an exploded perspective view of the two-layered patch 20 of FIG. 4, in reversed view. Patch 20 is provided with at least one outer impermeable layer 21, having an inner surface 201 and an outer surface 202. The inner surface 201 of at least one outer layer 21 is coated with an impermeable adhesive 23, as shown elsewhere in FIG. 4.

Patch 20 is also provided with an inner layer 22, having an inner surface 203 and an outer surface 204. Also shown is the tapering 17 of the at least one edge of at least one inner layer 22, so that patch 20 produces substantially no friction or mechanical interference when the patch undergoes movement relative to an adjacent surface with which the patch may be in slidable contact during sexual intercourse.

Also shown in release liner 18, which covers the inner surface of patch 20, protecting adhesive-coated surfaces 201 and 203 until release liner 18 is removed before the patch is adhered to the skin of the user. Release liner 18 is shown partially peeled back.

FIG. 6 is a perspective view of the flexible solid embodiment of the present invention (third embodiment). Flexible solid patch 30 is provided with at least one outer layer 31 having inner skin-facing surface 301 and outer surface 302 with an impermeable adhesive 33 on its inner surface. The adhesive coating 33 anchors the at least one outer layer 31 to the skin of the user and additionally anchors the at least one flexible solid layer 32, which comprises at least one inner layer 32, and is further comprised of a mixture of vasodilator and permeable adhesive, to the inner surface 301 of at least one outer layer 31. Inner at least one flexible solid layer 32 further has inner surface 303. At least one flexible solid layer 32 is adhered to inner surface 301 so as to be in contact with the skin of the user when the patch is in use. At least one flexible solid layer 32 allows inner surface 301, with peripheral area 320, coated with impermeable adhesive 330, to contact the skin of the user when the patch 30 is in use. Also shown is the tapering 17 of the at least one edge of at least one outer layer 31, so that the patch 30 produces substantially no friction or mechanical interference when the patch undergoes movement relative to an adjacent surface with which the patch may be in slidable contact during sexual intercourse.

Also shown is release liner 18, which covers the inner surface of patch 30, protecting adhesive-coated surfaces 301 and 303 until the release liner 18 is removed before the patch is adhered to the skin of the user. Release liner 18 is shown partially peeled back.

FIG. 7 is an exploded perspective view of the flexible solid patch 30 of FIG. 6, in reversed view. Patch 30 is provided with at least one outer impermeable layer 31, having an inner surface 301 and an outer surface 302. The inner surface 301 of at least one outer layer 31 is coated with an impermeable adhesive 33, as shown elsewhere in FIG. 6.

Patch 30 is also provided with inner layer 32, having an inner surface 303 and an outer surface 304. Also shown is the tapering 17 of the at least one edge of at least one inner layer 32, so that patch 30 produces substantially no friction or mechanical interference when the patch undergoes movement relative to an adjacent surface with which the patch may be in slidable contact during sexual intercourse.

Also shown is release liner 18, which covers the inner surface of patch 30, protecting surfaces 301 and 303 until the release liner 18 is removed before the patch is adhered to the skin of the user. Release liner 18 is shown partially peeled back.

FIG. 8 is a perspective view of a conventional condom, having an outside surface 40, an inside surface 41, an open end 42 and a closed end 43.

FIG. 9 is a cut-away perspective view of multi-layered condom-embodiment of the present invention (first condom embodiment), and FIG. 10 is a close-up perspective view of the same embodiment. Transdermal patch 10 includes three substrate layers including an at least one outer barrier layer 11, having a coating of adhesive on outer surface 102 for contact with and adhesive bonding to the inside surface 41 of the condom, and, as shown elsewhere in the drawings, an at least one middle layer 12 containing the vasodilator, and an at least one inner layer 13 constructed of a layer which contains a means for dispensing the vasodilator through the skin of the user, for example, a plastic film with microholes. Patch 10 is similar in construction to the multi-layered patch shown in FIGS. 1–3, except that the outer surface 102 of at least one outer barrier layer 11 has an adhesive coat 44 which attaches patch 10 to the inner surface 41 of the condom. At least one barrier layer 11 includes peripheral area 101, which extends beyond the perimeter of at least one inner layer 13 and at least one middle layer 12, which layers 12 and 13 are co-termimus in respect to each other's outer perimeters. Patch 10 is provided with release liner 18, which is shown partially peeled back.

FIG. 10 additionally shows transdermal patch 10 attached to inside surface 41 of condom 40. Inner surface 103 of inner layer 13 is provided with a permeable adhesive 15. The portion of inner surface 101 of outer barrier layer 11, extending circumferentially and/or radially beyond the inner layers, is peripheral area 120. Also shown is the tapering 17 of the edges of outer layer 11, middle layer 12 and inner layer 13.

The strength of the condom adhesive 44 coated upon outer surface 102 for contact with and adherence to condom inner surface 41 can be varied so that, selectively, in one variant patch 10 remains attached to the inner surface 41 of the condom during use, or in an alternate variant with a more releasable adhesive used upon surface 102, the patch 10 releases from the inner surface 41 of the condom during use, and this releasing of patch 10 permits the patch to move slidably relative to the inner surface of the condom. However, as in the patch of FIG. 1, the at least one barrier layer 11 is coated with an impermeable adhesive on its inner surface 101 that attaches to the skin of the penis and holds at least two inner layers 12 and 13 to the barrier layer. Whether or not patch 10 releases from the inner wall of the condom, patch 10 remains attached to the skin of the penis.

Figure 11:
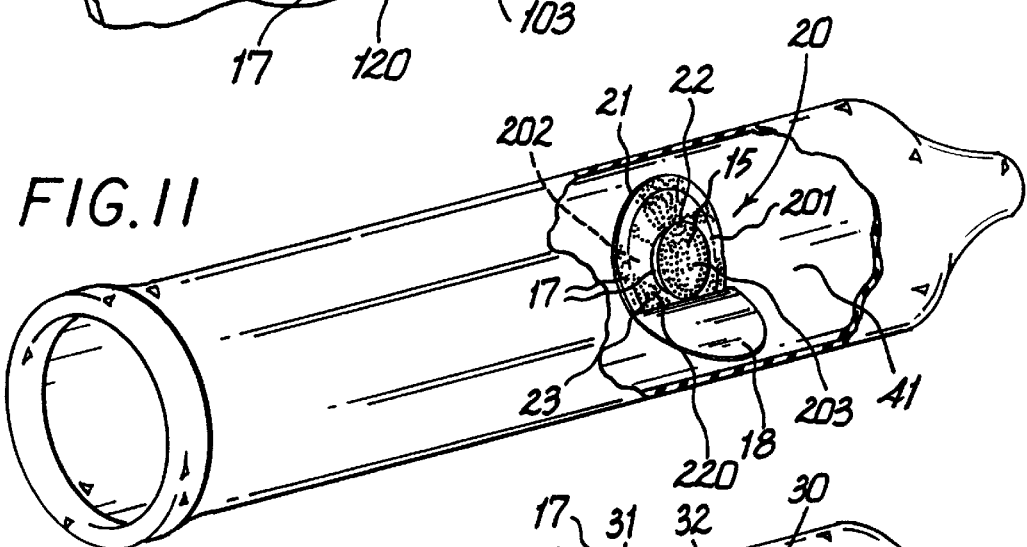
FIG. 11 is a cut-away, sectional view of the 2-layered condom-embodiment of the present invention.

FIG. 11 is a cross-sectional perspective view of 2-layered transdermal patch 20 (second condom embodiment). FIG. 11 shows a 2-layered patch analogous to that shown in FIG. 4, except that the patch of FIG. 11, being a condom embodiment, is provided with an adhesive coated upon out surface 202 for contact with and adherence to condom inner surface 41. In other respects, the patch of FIG. 11 is similar to that of FIG. 4, except that the strength of the condom adhesive coated upon outer surface 202 for contact with and adherence to condom inner surface 41 can be varied so that, selectively, in one variant patch 20 remains attached to the inner surface 41 of the condom during use, or in an alternate variant with a more releasable adhesive used upon surface 202, the patch 20 releases from the inner surface 41 of the condom during use, and this releasing of patch 20 permits the patch to move slidably relative to the inner surface of the condom. However, as in the patch of FIG. 4, the at least one barrier layer 21 is coated with an impermeable adhesive on its inner surface 201 that attaches to the skin of the penis and holds at least one inner layer 22 to the barrier layer. Whether or not patch 20 releases from the inner wall of the condom, patch 20 remains attached to the skin of the penis. Also shown is the tapering 17 of outer layer 21 and inner layer 22.

In addition to the two aforementioned variants, comprising different degrees of releasability of condom adhesive coated on outer surface 202 of the condom in the embodiment of FIG. 11, there is an additional variation which comprises the presence in one variant, and the absence in the alternate variant of permeable adhesive 15 on the inner surface 203 of the at least one inner layer 22. The variant in which adhesive 15 is omitted is not shown.

Figure 12:
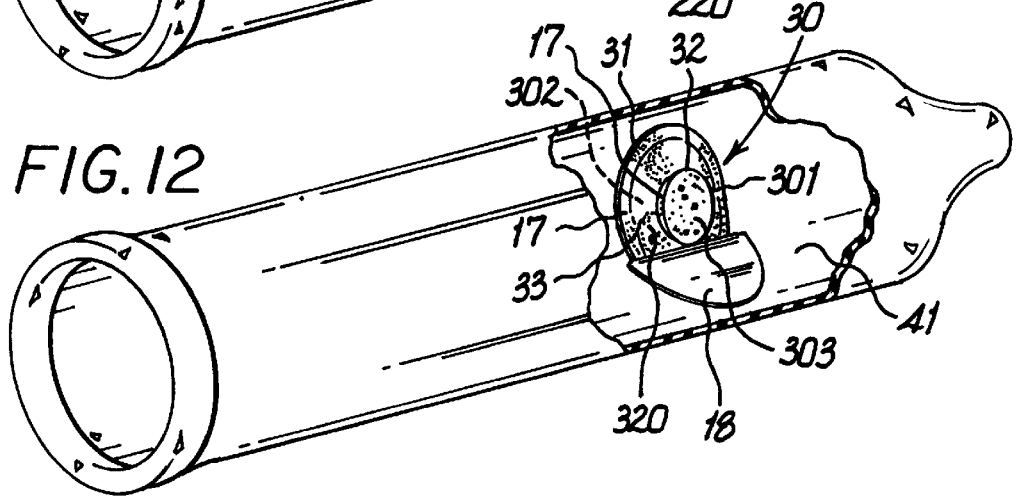
FIG. 12 is a cut-away, perspective view of the flexible solid condom-embodiment of the present invention.

FIG. 12 is a cut-away perspective view of the flexible solid condom-embodiment of the present invention (third condom embodiment). Flexible solid patch 30 is provided with an at least one inner layer 32 contacting the skin of the penis. An outer surface 302 of the at least one outer layer 31 is provided further with a coat of adhesive which contacts and adheres to the inner wall 41 of the condom and thereby anchors patch 30 to the inner wall of the condom. The strength of this adhesive coat upon outer surface 302 can be selected so as to provide two variants of condom patch 30. In one such variant patch 30 remains attached to the inner surface 41 of the condom during use, by virtue of having the adhesive coating upon surface 302 be a relatively strong adhesive. In an alternate variant, the adhesive coating upon surface 302 is made less strong, so that patch 30 permits the patch to move slidably relative to the inner surface of the condom. The inner surface 301 of the at least one barrier layer 31 is provided with a coating 33 of an impermeable adhesive that attaches to the skin of the penis and also secures at least one inner layer 32 to the barrier layer. The impermeable adhesive coating 33 on surface 301 comprises a coat upon peripheral area 320, which forms the outer part of surface 301.

At least one inner layer 32 is comprised of a permeable adhesive/vasodilator mixture, which comprises the flexible solid. The permeable adhesive component of the inner layer 32 serves to anchor the inner surface 303 of the flexible solid to the skin of the user.

Patch 30 is provided with a tapering 17 of the at least one edge of the at least one outer layer 31 and the at least one inner layer 32, so that patch 30 produces substantially no friction or mechanical interference when the patch undergoes movement relative to an adjacent surface with which the patch may be in slidable contact during sexual intercourse.

Also shown is release liner 18, which covers the inner surface of patch 30, protecting adhesive-coated surfaces 301 and 303 until the release liner 18 is removed before the patch is adhered to the skin of the user. Release liner 18 is shown partially peeled back.

FIGS. 13 and 13A are two views of the fourth condom-embodiment of the present invention. FIG. 13 is a cut-away perspective view of patch 50, which is adhesively attached to the inner surface 41 of the condom. FIG. 13A is an exploded view of the patch of FIG. 13. Patch 50 is provided with an at least one outer layer 51 which contains the vasodilator, and an at least one inner layer 52, which comprises a plastic film having microholes for regulating dispensing of vasodilator to the skin of the user. At least one outer layer 52 has an outer surface 502 and an inner surface 501 (shown in FIG. 13A). At least one inner layer 52 has an outer surface 504 (shown in FIG. 13A) and an inner surface 503. The inner surface 501 of at least one outer layer 53 is coated with a permeable adhesive 53, which anchors the at least one inner layer 52 to the at least one outer layer 51. The inner surface 503 of at least one inner layer 52 is also coated with a permeable adhesive, which anchors the at least one inner layer 52 to the skin of the penis. Outer surface 502 of the at least one outer layer 51 is provided with an adhesive that anchors patch 50 to the inner surface 41 of the condom. Also shown is the tapering 17 of the edges of the layers, so that patch 50 produces substantially no mechanical interference during sexual intercourse. Releasable liner 18 covers the inner surface of at least one inner layer 52, and is shown fully removed.

FIG. 14 is a cut-away perspective view of the fifth condom-embodiment of the present invention, showing flexible solid transdermal patch 60 adhesively attached to the inner surface 41 of the condom. Patch 60 is provided with one layer 60 which is comprised of a permeable adhesive/vasodilator mixture, which constitutes the flexible solid. The permeable adhesive component of the flexible solid anchors the patch to the skin of the penis. Also shown is the tapering 17 of the edges of the layers, so that patch 60 produces substantially no mechanical interference during sexual intercourse. Releasable liner 18 covers the inner surface of at least one inner layer 60, and is shown fully removed.

FIG. 15 shows a perspective view of a condom 40 having a transdermal patch in the form of an annular ring 70 disposed near and/or substantially at the closed end of the condom. Also shown is the tapering of the edges 17 of patch 70. The area occupied by annular ring transdermal patch 70 includes substantially less than one half of condom inner surface 41.

It is assumed that other modifications may be made to the present invention, without departing from the spirit and scope of the present invention, as noted in the appended claims.

I claim:

1. A method for treating male impotence by inducing a male penile erection on demand immediately before sexual intercourse comprising the steps of applying directly to the skin of a male user in the penile region thereof immediately prior to sexual intercourse a transdermal patch having adhesive application means for adhering the same to the male user's skin, said transdermal patch having an effective amount of treatment composition comprising a mixture of vasodilators, said transdermal patch having a dispensing means for dispensing said vasodilators only to the skin of the user in an effective amount sufficient to induce a male penile erection on demand immediately prior to sexual intercourse and barrier means for preventing contact of said vasodilator material with the internal genital tissues of the male user's sexual partner;

wherein further said vasodilator mixture comprises a mixture of papaverine, phentolamine and prostaglandin E-1.

2. The method for treating male impotence by inducing a male penile erection on demand immediately before sexual intercourse according to claim 1, wherein said transdermal patch comprises a plurality of layers with an inner layer for contacting the skin of the male user in the penile region including a reservoir for said vasodilator material and said dispensing means, and an outer barrier layer which completely envelopes said inner layer and said reservoir and extends beyond all the peripheral edges of said inner layer.

3. A method for treating male impotence by inducing a male penile erection on demand immediately before sexual intercourse comprising the steps of applying directly to the skin of a male user in the penile region thereof immediately prior to sexual intercourse a transdermal patch having adhesive application means for adhering the same to the male user's skin, said transdermal patch having an effective amount of treatment composition comprising a vasodilator, said transdermal patch having a dispensing means for dispensing said vasodilator only to the skin of the user in an effective amount sufficient to induce a male penile erection on demand immediately prior to sexual intercourse and barrier means for preventing contact of said vasodilator material with the internal genital tissues of the male user's sexual partner;

wherein said treatment composition comprises a vasodilator selected from the group consisting of papaverine, phentolamine and prostaglandin E-1;

said patch being an annular sleeve ring.

4. The method of inducing a male penile erection on demand immediately before sexual intercourse as in claim 1 wherein said means for dispensing said vasodilator through the penile region skin of the male user comprises a plastic film having microholes.

5. The method of inducing a male penile erection on demand immediately before sexual intercourse as in claim 1, wherein said transdermal patch is applied behind the scrotum of the user.

6. The method of inducing a male penile erection on demand immediately before sexual intercourse as in claim 5, wherein said transdermal patch is applied behind the scrotum.

7. A method for treating male impotence by inducing a male penile erection on demand immediately before sexual intercourse comprising the steps of applying directly to the skin of a male user in the penile region thereof immediately prior to sexual intercourse a transdermal patch having adhesive application means for adhering the same to the male user's skin, said transdermal patch having an effective amount of treatment composition comprising a vasodilator, said transdermal patch having a dispensing means for dispensing said vasodilator only to the skin of the user in an effective amount sufficient to induce a male penile erection on demand immediately prior to sexual intercourse and barrier means for preventing contact of said vasodilator material with the internal genital tissues of the male user's sexual partner, wherein said transdermal patch has therein an effective amount of a vasodilator treatment composition comprising about 10 milligrams of phentolamine mesylate dissolved in a suitable carrier, wherein there is a 50 percent transdermal transfer of said vasodilator across the thin scrotal skin of the penis, resulting in transfer of about 5 milligrams of said vasodilator therethrough.

8. The method as in claim 7 wherein said phentolamine mesylate is dissolved in a suitable carrier of about 0.230 milliliters of alcohol in said transdermal patch.

9. A method for treating male impotence by inducing a male penile erection on demand immediately before sexual intercourse comprising the steps of applying directly to the skin of a male user in the penile region thereof immediately prior to sexual intercourse a transdermal patch having adhesive application means for adhering the same to the male user's skin, said transdermal patch having an effective amount of a vasodilator treatment composition comprising a vasodilator, said transdermal patch having a dispensing means for dispensing said vasodilator only to the skin of the user in an effective amount sufficient to induce a male penile erection on demand immediately prior to sexual intercourse and barrier means for preventing contact of said vasodilator material with the internal genital tissues of the male user's sexual partner;

wherein said vasodilator comprises a mixture selected from the croup consisting of papaverine, phentolamine and prostaglandin E-1.

10. The method of inducing a male penile erection on demand, immediately before sexual intercourse as in claim 7 wherein said means for dispensing said vasodilator through the penile region skin of the male user comprises a plastic film having microholes.

11. The method for treating male impotence as in claim 9 wherein said transdermal patch comprises a plurality of layers with an inner layer for contacting the skin of the male user in the penile region including a reservoir for said vasodilator and said dispensing means therefor, and an outer barrier layer which completely envelopes said inner layer and said reservoir and extends beyond all the peripheral edges of said inner layer.

12. The method for treating male impotence as in claim 9 wherein said means for dispensing said vasodilator through the penile region of the male user comprises a plastic film having microholes.

13. A method for treating male impotence by inducing a male penile erection on demand immediately before sexual intercourse comprising the steps of applying directly to the skin of a male user in the penile region thereof immediately prior to sexual intercourse a transdermal patch having adhesive application means for adhering the same to the male user's skin, said transdermal patch having an effective amount of treatment composition comprising a vasodilator, said transdermal patch having a dispensing means for dispensing said vasodilator only to the skin of the user in an effective amount sufficient to induce a male penile erection on demand immediately prior to sexual intercourse and barrier means for preventing contact of said vasodilator material with the internal genital tissues of the male user's sexual partner, wherein said transdermal patch has therein an effective amount of a treatment composition such as a vasodilator comprising about 10 milligrams of phentolamine mesylate in a suitable carrier, wherein there is about a 50 percent transdermal transfer of about 5 milligrams of said vasodilator therethrough.

14. The method for treating male impotence as in claim 13 wherein said transdermal patch comprises a plurality of layers with an inner layer for contacting the skin of the male user in the penile region including a reservoir for said vasodilator and said dispensing means therefor, and an outer barrier layer which completely envelopes said inner layer and said reservoir and extends beyond all the peripheral edges of said inner layer.

15. The method for treating male impotence as in claim 13 wherein said means for dispensing said vasodilator through the penile region of the male user comprises a plastic film having microholes.

16. The method of inducing a male penile erection on demand immediately before sexual intercourse as in claim 9 wherein said transdermal patch is applied behind the scrotum of the user.

17. The method of inducing a male penile erection on demand immediately before sexual intercourse as in claim 13 wherein said transdermal patch is applied behind the scrotum of the user.

* * * * *